United States Patent
Allgeier et al.

(10) Patent No.: US 9,670,118 B2
(45) Date of Patent: *Jun. 6, 2017

(54) PRODUCTION OF ALPHA, OMEGA-DIOLS

(71) Applicant: E I DU PONT DE NEMOURS AND COMPANY, Wilmington, DE (US)

(72) Inventors: Alan Martin Allgeier, Wilmington, DE (US); Torren Ryan Carlson, Newark, DE (US); David Richard Corbin, West Chester, PA (US); Wathudura Indika Namal De Silva, Rahway, NJ (US); Carl Andrew Menning, Newark, DE (US); Joachim C Ritter, Wilmington, DE (US); Sourav Kumar Sengupta, Wilmington, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/877,507

(22) Filed: Oct. 7, 2015

(65) Prior Publication Data

US 2016/0023975 A1 Jan. 28, 2016

Related U.S. Application Data

(62) Division of application No. 13/870,066, filed on Apr. 25, 2013, now Pat. No. 9,018,423.

(60) Provisional application No. 61/639,404, filed on Apr. 27, 2012.

(51) Int. Cl.
   *C07C 29/132* (2006.01)
   *C07C 29/60* (2006.01)
   *C07C 209/16* (2006.01)

(52) U.S. Cl.
   CPC ............ *C07C 29/132* (2013.01); *C07C 29/60* (2013.01); *C07C 209/16* (2013.01)

(58) Field of Classification Search
   None
   See application file for complete search history.

(56) References Cited

U.S. PATENT DOCUMENTS

| | | |
|---|---|---|
| 2,201,347 A | 5/1940 | Rittmeister |
| 2,440,929 A | 5/1948 | Frederick |
| 2,768,213 A | 10/1956 | Whetstone et al. |
| 3,070,633 A | 12/1962 | Utne et al. |
| 3,083,236 A | 3/1963 | Utne et al. |
| 3,189,651 A | 6/1965 | Ellery et al. |
| 3,215,742 A | 11/1965 | Horlenko et al. |
| 3,223,714 A | 12/1965 | Manly et al. |
| 3,268,588 A | 8/1966 | Horlenko et al. |
| 3,270,059 A | 8/1966 | Winderl et al. |
| 2,082,025 A | 6/1973 | Peters, Jr. |
| 3,917,707 A | 11/1975 | Williams et al. |
| 3,933,930 A | 1/1976 | Dougherty |
| 4,254,059 A | 3/1981 | Grey |
| 4,400,468 A | 8/1983 | Faber |
| 4,401,823 A | 8/1983 | Arena |
| 4,780,552 A | 10/1988 | Wambach et al. |
| 5,030,771 A | 7/1991 | Fuhrmann et al. |
| 5,112,994 A | 5/1992 | Koseki et al. |
| 5,210,335 A | 5/1993 | Schuster et al. |
| 5,412,111 A | 5/1995 | Matsumoto et al. |
| 5,538,891 A | 7/1996 | Schneider et al. |
| 5,696,303 A | 12/1997 | Darsow et al. |
| 5,981,769 A | 11/1999 | Baur et al. |
| 6,008,418 A | 12/1999 | Baur et al. |
| 6,087,296 A | 7/2000 | Harper et al. |
| 6,147,208 A | 11/2000 | Achhammer et al. |
| 6,265,602 B1 | 7/2001 | Voit et al. |
| 6,403,845 B1 | 6/2002 | Pfeffinger et al. |
| 6,407,294 B1 | 6/2002 | Breitscheidel et al. |
| 6,433,192 B1 | 8/2002 | Fischer et al. |
| 6,462,220 B1 | 10/2002 | Luyken et al. |
| 6,593,481 B1 | 7/2003 | Manzer |
| 6,818,781 B2 | 11/2004 | Bhatia |

(Continued)

FOREIGN PATENT DOCUMENTS

| | | |
|---|---|---|
| CA | 2800797 A1 | 12/2011 |
| CN | 1039243 A | 1/1990 |

(Continued)

OTHER PUBLICATIONS

Abe, R. et al, "Photocatalytic overall water splitting under visible light by TaON and WO3 with an IO3-/I-shuttle redox mediator", Chem Commun, 2005, 3829-3831.
Adkins, H. et al, "The catalytic hydrogenation of organic compounds over copper chromite", J Am Chem Soc (1931), vol. 53, 1093.
Alexeev, O.S. et al, "gamma-Al2O3-Supported Pt catalysts with extremely high dispersions resulting from Pt-W interactions", J Catal, 190 (2000) 157-17.
Binder et al., "Simple chemical transformation of lignocellulosic biomass into furans for fuels and chemicals", J Am Chem Soc (2009) 131, 1979-1985.
Blanc, B. et al, "Starch-derived polyols for polymer technologies: preparation by hydrogenolysis on metal catalysts", Green Chemistry, Apr. 2000, 89-91.
Buntara, T. et al, "Caprolactam from Renewable Resources: Catalytic Conversion of 5-Hydroxymethylfurfural into Caprolactone", Angew. Chem. Int. Ed. (2011), 50(31), 7083-7087.

(Continued)

Primary Examiner — Brian J Davis

(57) ABSTRACT

Disclosed herein are processes for preparing an $\alpha,\omega$-$C_n$-diol, wherein n is 5 or greater, from a feedstock comprising a $C_n$ oxygenate. In one embodiment, the process comprises contacting the feedstock with hydrogen gas in the presence of a catalyst comprising Pt, Cu, Ni, Pd, Pt, Rh, Ir, Ru, or Fe on a $WO_3$ or $WO_x$ support. In one embodiment, the process comprises contacting the feedstock with hydrogen in the presence of a catalyst comprising a metal M1 and a metal M2 or an oxide of M2, and optionally a support. In one embodiment, M1 is Pd, Pt, or Ir; and M2 is Mo, W, V, Mn, Re, Zr, Ni, Cu, Zn, Cr, Ge, Sn, Ti, Au, or Co. The $C_n$ oxygenate may be obtained from a biorenewable resource.

10 Claims, No Drawings

(56) References Cited

U.S. PATENT DOCUMENTS

| | | |
|---|---|---|
| 7,019,155 B2 | 3/2006 | Manzer |
| 7,064,239 B2 | 6/2006 | Fischer et al. |
| 7,230,145 B2 | 6/2007 | Kadowaki et al. |
| 7,994,347 B2 | 8/2011 | Lilga et al. |
| 8,053,608 B2 | 11/2011 | Kouno et al. |
| 8,053,615 B2 | 11/2011 | Cortright et al. |
| 8,188,321 B2 | 5/2012 | Suzuki et al. |
| 8,222,463 B2 | 7/2012 | Kalnes et al. |
| 8,263,792 B2 | 9/2012 | Robinson |
| 8,378,152 B2 | 2/2013 | Kouno et al. |
| 8,471,042 B2 | 6/2013 | Pinkos et al. |
| 8,501,989 B2 | 8/2013 | Boussie et al. |
| 8,524,924 B2 | 9/2013 | Burket et al. |
| 8,524,925 B2 | 9/2013 | Sabesan et al. |
| 8,536,349 B2 | 9/2013 | Bevinakatti et al. |
| 8,629,306 B2 | 1/2014 | Pinkos et al. |
| 8,642,790 B2 | 2/2014 | Reichert et al. |
| 8,642,813 B2 | 2/2014 | Qiao et al. |
| 8,669,393 B2 | 3/2014 | Boussie et al. |
| 8,759,594 B2 | 6/2014 | Abillard et al. |
| 8,796,477 B2 | 8/2014 | Janka et al. |
| 8,809,605 B2 | 8/2014 | Bao et al. |
| 8,846,984 B2 | 9/2014 | Allgeier et al. |
| 8,846,985 B2 | 9/2014 | Allgeier et al. |
| 8,853,458 B2 | 10/2014 | Dias et al. |
| 8,859,826 B2 | 10/2014 | Allgeier et al. |
| 8,865,940 B2 | 10/2014 | Allgeier et al. |
| 8,884,035 B2 | 11/2014 | De Silva et al. |
| 8,884,036 B2 | 11/2014 | De Silva et al. |
| 8,889,912 B2 | 11/2014 | Allgeier et al. |
| 8,889,922 B2 | 11/2014 | Allgeier et al. |
| 8,962,894 B2 | 2/2015 | Allgeier et al. |
| 8,981,130 B2 | 3/2015 | De Silva et al. |
| 9,018,423 B2 | 4/2015 | Allgeier et al. |
| 9,024,047 B2 | 5/2015 | Kasat et al. |
| 9,035,098 B2 | 5/2015 | Feist et al. |
| 9,045,382 B2 | 6/2015 | Pinkos et al. |
| 2003/0212298 A1 | 11/2003 | Brasse et al. |
| 2006/0014988 A1 | 1/2006 | Fischer et al. |
| 2007/0287845 A1 | 12/2007 | Lilga et al. |
| 2008/0200698 A1 | 8/2008 | Reichert et al. |
| 2009/0156841 A1 | 6/2009 | Sanborn et al. |
| 2009/0314992 A1 | 12/2009 | Pinkos et al. |
| 2010/0113841 A1 | 5/2010 | Suzuki et al. |
| 2010/0216958 A1 | 8/2010 | Peters et al. |
| 2010/0274030 A1 | 10/2010 | Bevinakatti et al. |
| 2010/0317822 A1 | 12/2010 | Boussie et al. |
| 2011/0040131 A1 | 2/2011 | Kouno et al. |
| 2011/0071306 A1 | 3/2011 | Robinson |
| 2011/0218318 A1 | 9/2011 | Boussie et al. |
| 2011/0263916 A1 | 10/2011 | Bao et al. |
| 2011/0312051 A1 | 12/2011 | Kalnes et al. |
| 2012/0010419 A1 | 1/2012 | Pinkos et al. |
| 2012/0022298 A1 | 1/2012 | Pinkos et al. |
| 2012/0035399 A1 | 2/2012 | Abillard et al. |
| 2012/0059174 A1 | 3/2012 | Abillard et al. |
| 2012/0116122 A1 | 5/2012 | Feist et al. |
| 2012/0172579 A1 | 7/2012 | Qiao et al. |
| 2013/0172578 A1 | 7/2013 | Allgeier et al. |
| 2013/0172579 A1 | 7/2013 | Desilva et al. |
| 2013/0172580 A1 | 7/2013 | Ritter et al. |
| 2013/0172586 A1 | 7/2013 | Desilva et al. |
| 2013/0172629 A1 | 7/2013 | Allgeier et al. |
| 2013/0184495 A1 | 7/2013 | Dias et al. |
| 2013/0231505 A1 | 9/2013 | Allgeier et al. |
| 2013/0289311 A1 | 10/2013 | Allgeier et al. |
| 2013/0289312 A1 | 10/2013 | Allgeier et al. |
| 2013/0289318 A1 | 10/2013 | Allgeier et al. |
| 2013/0289319 A1 | 10/2013 | Allgeier et al. |
| 2014/0081065 A1 | 3/2014 | Sengupta et al. |
| 2014/0228596 A1 | 8/2014 | Allgeier et al. |
| 2015/0099903 A1 | 4/2015 | Allgeier et al. |

FOREIGN PATENT DOCUMENTS

| | | |
|---|---|---|
| CN | 1890231 A | 1/2007 |
| CN | 101279892 A | 10/2008 |
| CN | 101628875 A | 1/2010 |
| CN | 102015702 A | 4/2011 |
| CN | 102190639 A | 9/2011 |
| DE | 4238493 C1 | 4/1994 |
| EP | 110089 B1 | 1/1988 |
| EP | 0411403 A1 | 2/1991 |
| EP | 0418925 A2 | 3/1991 |
| EP | 1243573 A1 | 9/2002 |
| EP | 1243673 A1 | 9/2002 |
| EP | 2138478 A1 | 12/2009 |
| EP | 2390247 A1 | 11/2011 |
| JP | 04041449 A | 2/1992 |
| JP | 04046133 A | 2/1992 |
| JP | 2001-226303 A | 8/2001 |
| JP | 2003183200 A | 7/2003 |
| JP | 2006036653 A | 2/2006 |
| JP | 04555475 B2 | 9/2010 |
| KR | 100645668 B1 | 11/2006 |
| KR | 100688765 B1 | 2/2007 |
| WO | 9955654 A1 | 11/1999 |
| WO | 2007103586 A2 | 9/2007 |
| WO | 2007103586 A3 | 9/2007 |
| WO | 2009126852 A1 | 10/2009 |
| WO | 2009133787 A1 | 11/2009 |
| WO | 2010033789 A2 | 3/2010 |
| WO | 2010033789 A3 | 3/2010 |
| WO | 2010062689 A2 | 6/2010 |
| WO | 2010099201 A1 | 9/2010 |
| WO | 2010115759 A2 | 10/2010 |
| WO | 2010115759 A3 | 10/2010 |
| WO | 2010144873 A1 | 12/2010 |
| WO | 2011149339 A1 | 12/2011 |
| WO | 2013027766 A1 | 2/2013 |
| WO | 2013066776 A1 | 5/2013 |
| WO | 2013109477 A1 | 7/2013 |
| WO | 2014047435 A1 | 3/2014 |
| WO | 2014159484 A1 | 10/2014 |
| WO | 2014159490 A1 | 10/2014 |

OTHER PUBLICATIONS

Buntara, T. et al., "From 5-hydroxymethylfurfural (HMF) to polymer precursors: catalyst screening studies on the conversion of 1,2,6-hexanetriol to 1,6-hexanediol", Top Catal (2012) 55, 612-619.
Caes et al., "Conversion of Fructose into 5-(Hydroxymethyl)furfural in Sulfolane", ChemSusChem, (2011), 4(3), 353-356.
Chen, K. et al, "Chemoselective hydrogenolysis of tetrahydropyran-2-methanol to 1,6-hexanediol over rhenium-modified carbon-supported rhodium catalysts", ChemCatChem (2010) 2, 547-555.
Chen, K. et al, "C—O bond hydrogenolysis of cyclic ethers with OH groups over rhenium-modified supported iridium catalysts", J Catalysis (2012) vol. 294, 171-183.
Corma, A. "Inorganic Solid Acids and Their Use in Acid-Catalyzed Hydrocarbon Reactions", (1995) Chem. Rev., 95, 559-614.
Diebold, U. "The surface science of titanium dioxide", Surface Science Reports 48 (2003) 53-229.
Efremov, A.A. et al, "Conversions of Levoglucosenone in Acid Media", Sibirskii Khimicheskii Zhurnal 1992, 6, 34-39 Translation.
Efremov, A.A., "Transformations of levoglucosenone at the anhydroglucoside bond", Chem Natural Compounds (1998) 34, 5, 582-589.
Efremov, A.A. et al, "New thermocatalytic methods of chemicals producing from lignocellulosic materials in the presence of acid-type catalysts", Intl Symposium Wood Pulping Chemistry, 8th, Helsinki (1995) 689-696.
French, G.J. et al, "A re-investigation of the thermal decomposition of ammonium paratungstate", J. Mat. Sci, 16 (1981) 3427-3436.
Gong, L. et al, "Selective hydrogenolysis of glycerol to 1,3-propanediol over a Pt/WO3/TiO2/SiO2 catalyst in aqueous media", Appl Catal A General 390 (2010) 119-126.
Gong, X.Q. et al, "Small Au and Pt Clusters at the Anatase TiO2(101) Surface: Behavior at Terraces, Steps, and Surface Oxygen Vacancies", J. Am. Chem. Soc. 130 (2008) 370-381.

(56) References Cited

OTHER PUBLICATIONS

Helberger et al, Justus Liebigs Annalen der Chemie (1949) 561, 215-220.
Huang, L. et al, "Direct conversion of glycerol into 1,3-propanediol over Cu—H4SiW12O40/SiO2 in vapor phase", Catal Lett, 131 (2009) 312-320.
Jae, J. et al, "Investigation into the shape selectivity of zeolite catalysts for biomass conversion", Journal of Catalysis (2011) 279, 257-268.
Jalil, P.A. et al, "A Study of Stability of Tungstophosphoric Acid, H3PW12O40, Using Synchrotron XPS, XANES, Hexane Cracking, XRD and IR Spectroscopy", J. Catalysis, 2003, 217(2), 292-297.
Jayaraman, S. et al, "Synthesis and Characterization of Pt-WO3 as Methanol Oxidation Catalysts for Fuel Cells", J Phys Chem B, 2005, 109, 22958-22966.
Jung, M.E. et al, "Synthesis of Methylene-Expanded 2',3'-Dideoxyribonucleosides", J Organic Chemistry 63 (1998) 8133-8144.
Kamalakar, G. et al, "tert-Butylation of Phenol over Ordered Solid Acid Catalysts in Supercritical Carbon Dioxide: Efficient Synthesis of 2,4-Di-tert-butylphenol and 2,4,6-Tri-tert-butylphenol", Ind Eng Chem Res, 45 (2006) 6118-6126.
Karinen, R. et al, "Biorefining: heterogeneously catalyzed reactions of carbohydrates for the production of furfural and hydroxymethyfurfural", Chem Sus Chem (2011) 4, 1002-1016.
Kaufmann, W.E. et al, "The use of platinum oxide as a catalyst in the reduction of organic compounds. IV. Reduction of furfural and its derivatives", J Am Chem Soc (1923) 45, 3029-3044.
Kiss, A.B. et al, "Thermal polycondensation of ammonium paratungstate, (NH4)10[W12O40(OH)2].4H2O", J. Materials Sci, 13 (1978) 2541-2547.
Koso, S. et al, "Chemoselective hydrogenolysis of tetrahydrofurfuryl alcohol to 1,5-pentanediol", Chem. Commun. (2009) 2035-2037.
Koso, S. et al, "Promoting effect of Mo on the hydrogenolysis of tetrahydrofurfuryl alcohol to 1,5-pentanediol over Rh/SiO2", J Catalysis 267 (2009), 89-92.
Kuba, S. et al, "Structure and properties of tungstated zirconia catalysts for alkane conversion", J Catalysis, 216 (2003) 353-361.
Lee, U. et al, "Structure of pentasodium trihydrogenhexatungstoplatinate(IV) icosahydrate", Acta Cryst. (1983) C39, 817-819.
Li, N.; Huber, G.W., "Aqueous-phase hydrodeoxygenation of sorbitol with Pt/SiO2-Al2O3: identification of reaction intermediates", Journal of Catalysis (2010) 270, 48-59.
Li, N. et al, "Renewable gasoline from aqueous phase hydrodeoxygenation of aqueous sugar solutions prepared by hydrolysis of maple wood", Green Chemistry 2011, 13, 91-101.
Liu, L. et al, "Mesoporous WO3 supported Pt catalyst for hydrogenolysis of glycerol to 1,3-propanediol", Chin. J Catal., 2012, 33, 1257-1261.
Miftakhov, M.S. et al, "Levoglucosenone: the properties, reactions, and use in fine organic synthesis", Russian Chem Reviews (1994) 63(10) 869-882.
Nakagawa, Y. et al, "Heterogeneous catalysis of the glycerol hydrogenolysis", Catal Sci Technol 2011, 1, 179-190.
Nakagawa, Y. et al., "Production of 1,5-pentanediol from biomass via furfural and tetrahydrofurfuryl alcohol", Catalysis Today 195 (2012) 136-143.
Nikolla, E. et al., "'One-Pot' Synthesis of 5-(Hydroxymethyl)furfural from Carbohydrates Using Tin-Beta Zeolite", ACS Catal. (2011), 1, 408-410.
Okuhara, T. et al, "Insoluble heteropoly compounds as highly active catalysts for liquid-phase reactions", J. Mol. Catal. 74 (1992) 247-256.
Ott, L. et al, "Catalytic Dehydration of Glycerol in sub- and supercritical water: a new chemical process for acrolein production", Green Chemistry, 2006, pp. 214-220, vol. 8.
Pae, Y.I. et al, "Characterization of NiO—TiO2 modified with WO3 and catalytic activity for acid catalysis", Bull. Korean Chem. Soc. 2004, vol. 25(12), 1881-1888.
Ponder, G. R. et al, "Pyrolytic Conversion of Biomass of Anhydrosugars—Influences of Indigenous Ions and Polysaccharide Structures", Applied Biochem Biotech, 1990, vol. 24/25, p. 41-47.
Roman-Leshkov, Y. et al., "Solvent effects on fructose dehydration to 5-hydroxymethylfurfural in biphasic systems saturated with inorganic salts", Top Catal (2009) 52:297-303.
Shafizadeh, F. et al., Some Reactions of Levoglucosenone, Carbohydrate Research, 1979, pp. 169-191, vol. 71.
SRI Process Economics Program, 31, Hexamethylenediamine Nov. 1967.
Ten Dam, J. et al, "Pt/Al2O3 catalyzed 1,3-propanediol formation from glycerol using tungsten additives", ChemCatChem (2013), 5(2), 497-505.
Tong, X. et al, "Biomass into chemicals: conversion of sugars to furan derivatives by catalytic processes", Appl. Catalysis A General, 385 (2010) 1-13.
Tripathy, P.K. et al, "A comparative study on the thermal decomposition of ammonium p-tungstate in batch and fluidized-bed reactors", Ind Eng Chem Res 36 (1997) 3602-3606.
Trost, B. M. "Cyclizations Made Easy by Transition Metal Catalysts", in Homogeneous Transition Metal Catalyzed Reactions; Moser, W. et al; Adv. Chem. 31, 1992, ACS, Washington, DC, p. 463-478.
Xu, W. et al, "Direct catalytic conversion of furfural to 1,5-pentanediol by hydrogenolysis of the furan ring under mild conditions over Pt/Co2AlO4 catalyst" Chem Comm, Royal Society of Chemistry (2011) vol. 47, No. 13, 3924-3926.
Yamazoe, S. et al, "XAFS Study of Tungsten L1-, L3-Edges: Structural Analysis of Loaded Tungsten Oxide Species", Envir Sci, Research Frontiers 2008, Spring 8, 138-139.
Yamazoe, S. et al, "XAFS Study of Tungsten L1- and L3-Edges: Structural Analysis of WO3 Species Loaded on TiO2 as a Catalyst for Photo-oxidation of NH3", J. Phys Chem C 2008, 112, 6869-6879.
Yoshinaga, Y. et al, "Shape-selective oxidation catalysed by a Pt-promoted ultramicroporous heteropoly compound", J.Chem. Soc. Faraday Trans 1998, 94(15) 2235-2240.
Zanardi, M.M. et al, "Synthesis of a simple chiral auxiliary derived from levoglucosenone and its application in a Diels-Alder reaction", Tetrahedron letters 50 (2009) 999-1002.
Alamillo, R. et al., "Selective Hydrogenation of Biomass-Derived 5-Hydroxymethylfurfural Using Heterogeneous Catalysts", Green Chem., 2012, 14, 1413.
Jung, K.J. et al., "Furfural Decarbonylation Catalyzed by Charcoal Supported Palladium: Part I—Kinetics", Biomass 16 (1988) 63-76.
Jung, K.J. et al., "Furfural Decarbonylation Catalyzed by Charcoal Supported Palladium: Part II—A Continuous Process", Biomass 16 (1988) 89-96.
International Search Report dated Mar. 29, 2013, PCT/US2012/062314.
International Search Report dated Apr. 29, 2013, PCT/US2012/071891.
International Search Report dated Apr. 29, 2013, PCT/US2012/071907.
International Search Report dated Apr. 29, 2013, PCT/US2012/071893.
International Search Report dated Apr. 29, 2013, PCT/US2012/071912.
International Search Report dated Apr. 30, 2013, PCT/US2012/071894.
International Search Report dated Jul. 26, 2013, PCT/US2013/038403.
International Search Report dated Jul. 18, 2013, PCT/US2013/038418.
International Search Report dated Jul. 24, 2013, PCT/US2013/038441.
International Search Report dated Jul. 24, 2013, PCT/US2013/038436.
Office actions dated Jun. 26, 2013; Sep. 13, 2013; and May 7, 2014 for U.S. Appl. No. 13/729,390.

(56) References Cited

OTHER PUBLICATIONS

Office action dated Dec. 20, 2013 for U.S. Appl. No. 13/729,507.
Office action dated Apr. 9, 2014 for U.S. Appl. No. 13/870,080.
Database CAPLUS on STN, AN 1979:151575, Nishino et al, JP 53149905 A, Dec. 27, 1978 (abstract).
Database WPIX on STN, AN 1979-11181B [197906], Nishino et al, JP53149905 A Dec. 27, 1978 (abstract).
International Preliminary Report on Patentability, PCT International Application PCT/US2012/062314 dated May 6, 2014.
International Preliminary Report on Patentability, PCT International Application PCT/US2012/071891 dated Jul. 1, 2014.
International Preliminary Report on Patentability, PCT International Application PCT/US2012/071907 dated Jul. 1, 2014.
International Preliminary Report on Patentability, PCT International Application PCT/US2012/071893 dated Jul. 1, 2014.
International Preliminary Report on Patentability, PCT International Application PCT/US2012/071912 dated Jul. 1, 2014.
International Preliminary Report on Patentability, PCT International Application PCT/US2012/071894 dated Jul. 1, 2014.
International Preliminary Report on Patentability, PCT International Application PCT/US2013/038403 dated Oct. 28, 2014.
International Preliminary Report on Patentability, PCT International Application PCT/US2013/038418 dated Oct. 28, 2014.
International Preliminary Report on Patentability, PCT International Application PCT/US2013/038436 dated Oct. 28, 2014.
International Preliminary Report on Patentability, PCT International Application PCT/US2013/038441 dated Oct. 28, 2014.
Qin, L.-Z. et al., "Aqueous-phase deoxygenation of glycerol to 1,3-propanediol over Pt/WO3/ZrO2 catalysts in a fixed-bed reactor", Green Chem., 2010, 12, 1466-1472.
Rao, R.S. et al., "Furfural Hydrogenation Over Carbon-Supported Copper", Catalysis Letters 60 (1999) 51-57.
Zheng, H.-Y. et al., "Towards Understanding the Reaction Pathway in Vapour Phase Hydrogenation of Furfural to 2-Methylfuran", J Molecular Catalysis A: Chemical 246 (2006) 18-23.
Chia, Mei et al., Selective Hydrogenolysis of Polyols and Cyclic Ethers over Bifunctional Surface Sites on Rhodium-Rhenium Catalysts, J. Am. Chem. Soc, 2011, 12675-12689, 133.

PRODUCTION OF ALPHA, OMEGA-DIOLS

This application claims priority under 35 U.S.C. §119(e) from, and claims the benefit of, U.S. Provisional Application No. 61/639,404 filed Apr. 27, 2012, which is by this reference incorporated in its entirety as a part hereof for all purposes.

FIELD OF DISCLOSURE

The present invention relates to processes for preparing alpha, omega-diols ("α,ω-diols"). More particularly, the present invention relates to processes for preparing α,ω-diols by selective hydrodeoxygenation of oxygenated compounds which can be derived from carbohydrates or biologic sources.

BACKGROUND

The α,ω-diols such as 1,5-pentanediol and 1,6-hexanediol are useful as chemical intermediates for the production of agrichemicals, pharmaceuticals, and polymers. For example, α,ω-diols can be used as plasticizers and as comonomers in polyesters and polyether-urethanes. It has become increasingly desirable to obtain industrial chemicals such as α,ω-diols, or their precursors, from materials that are not only inexpensive but also benign in the environment. Of particular interest are materials which can be obtained from renewable sources, that is, materials that are produced by a biological activity such as planting, farming, or harvesting. As used herein, the terms "renewable" and "biosourced" can be used interchangeably.

Biomass sources for such materials are becoming more attractive economically versus petroleum-based ones. Although the convergent and selective synthesis of $C_5$ and $C_6$ carbocyclic intermediates from biomass is difficult because of the high degree of oxygenation of many components of biomass, use of such biomass-derived intermediates as feedstocks would offer new routes to industrially useful chemicals.

1,6-Hexanediol is a useful intermediate in the industrial preparation of nylon 66. 1,6-Hexanediol can be converted by known methods to 1,6-hexamethylene diamine, a starting component in nylon production. 1,6-Hexanediol is typically prepared from the hydrogenation of adipic acid or its esters or the hydrogenation of caprolactone or its oligomers. For example, in WO 2011/149339, deVries J-G, et al describe a process for the preparation of caprolactone, caprolactam, 2,5-tetrahydrofuran-dimethanol, 1,6-hexanediol or 1,2,6-hexanetriol from 5-hydroxymethyl-2-furfuraldehyde and teach that 1,2,6-hexanetriol may be hydrogenated to 1,6-hexanediol using a catalyst based on palladium, nickel, rhodium, ruthenium, copper and chromium or mixtures thereof. Further, the catalysts may be doped with one or more other elements, such as rhenium.

JP 2003-183200 teaches a method for preparation of 2,5-diethyl-1,6-hexanediol from tetrahydropyran derivatives, e.g. 2,5-diethyltetrahydropyran-2-methanol, comprising hydrogenation of the starting material in the presence of a metal catalyst carried on an acidic support, notably 5% Pt/$Al_2O_3$ and 5% Pt/$SiO_2$—$Al_2O_3$ at 200-240° C. Yields ranged from 40 to 61%.

There is an existing need for processes to make α,ω-diols, especially $C_5$ and $C_6$ α,ω-diols, and synthetic intermediates useful in the production of α,ω-diols, from renewable biosources. There is an existing need for processes to produce 1,5-pentanediol, 1,6-hexanediol, and other α,ω-diols at high yield and high selectivity from biomass-derived starting materials, including 1,2,6-hexanetriol, tetrahydrofuran-2,5-dimethanol, and 2-hydroxymethyltetrahydropyran.

SUMMARY

In one embodiment, a process for preparing an α,ω-$C_n$-diol is provided, the process comprising the steps:
(a) providing a feedstock comprising a $C_n$ oxygenate;
(b) contacting the feedstock with hydrogen gas, in the presence of a catalyst at a temperature and for a time sufficient to form a product mixture comprising α,ω-$C_n$-diol; wherein n is 5 or greater; and wherein the catalyst comprises Pt, Cu, Ni, Pd, Rh, Ir, Ru, or Fe on a $WO_3$ or $WO_x$ support.

In another embodiment, a process for preparing an α,ω-$C_n$-diol is provided, the process comprising the steps:
(a) providing a feedstock comprising a $C_n$ oxygenate;
(b) contacting the feedstock with hydrogen gas, in the presence of a catalyst at a temperature and for a time sufficient to form a product mixture comprising an α,ω-$C_n$-diol; wherein n is 5 or greater;
and wherein the catalyst comprises a metal M1 and a metal M2 or an oxide of M2, and optionally a support, wherein:
  M1 is Pd, Pt, or Ir; and M2 is Mo, W, V, Mn, Re, Zr, Ni, Cu, Zn, Cr, Ge, Sn, Ti, Au, or Co; or
  M1 is Rh and M2 is Mo, W, V, Mn, Ni, Cu, Zn, Cr, Ge, Sn, Ti, Au, or Zr; or
  M1 is Ag, Au or Co; and M2 is Re, Mo, or W; or
  M1 is Cu, Pd, Fe, or Ni; and M2 is Re, Mo, Cu, Zn, Cr, Ge, Sn, or W; or
  M1 is Ag, Pt, Cu, or Au, and M2 is Ni, Fe, Sn, Ge, or Ir; or
  M1 is Co and M2 is Fe; or
  M1 is Ni and M2 is Co or Fe; or
  M1 is Mn and M2 is Cr.

DETAILED DESCRIPTION

As used herein, where the indefinite article "a" or "an" is used with respect to a statement or description of the presence of a step in a process disclosed herein, it is to be understood, unless the statement or description explicitly provides to the contrary, that the use of such indefinite article does not limit the presence of the step in the process to one in number.

As used herein, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the term "about" modifying the quantity of an ingredient or reactant employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. The term "about" may mean within 10% of the reported numerical value, preferably within 5% of the reported numerical value.

As used herein, the term "organic compound" means a carbon-containing compound with the following exceptions: binary compounds as the carbon oxides, carbides, carbon disulfide, etc.; ternary compounds such as metallic cyanides, metallic carbonyls, phosgene, carbonylsulfide; and metallic carbonates such as calcium carbonate and sodium carbonate.

As used herein, the term "oxygenate" means an organic compound containing at least one oxygen atom. As used herein, the term "$C_n$ oxygenate" means an oxygenate containing n carbon atoms and, analogously, the term "$C_n$ diol" denotes a diol containing n carbon atoms.

As used herein, the term "biomass" refers to any cellulosic or lignocellulosic material and includes materials comprising hemicellulose, and optionally further comprising lignin, starch, oligosaccharides and/or monosaccharides.

As used herein, the term "lignocellulosic" means comprising both lignin and cellulose. Lignocellulosic material may also comprise hemicellulose. In some embodiments, lignocellulosic material contains glucan and xylan.

As used herein, the term "hemicellulose" means a non-cellulosic polysaccharide found in lignocellulosic biomass. Hemicellulose is a branched heteropolymer consisting of different sugar monomers. It typically comprises from 500 to 3000 sugar monomeric units.

As used herein, the term "lignin" refers to a complex high molecular weight polymer that can comprise guaiacyl units, as in softwood lignin, or a mixture of guaiacyl and syringyl units, as in hardwood lignin.

As uses herein, the term "starch" refers to a carbohydrate consisting of a large number of glucose units joined by glycosidic bonds. Starch, also known as amylum, typically contains amylose and amylopectin.

As used herein, the term "sugar" includes monosaccharides, disaccharides, and oligosaccharides. Monosaccharides, or "simple sugars," are aldehyde or ketone derivatives of straight-chain polyhydroxy alcohols containing at least three carbon atoms. A pentose is a monosaccharide having five carbon atoms; examples include xylose, arabinose, lyxose, and ribose. A hexose is a monosaccharide having six carbon atoms; examples include glucose and fructose. Disaccharide molecules consist of two covalently linked monosaccharide units; examples include sucrose, lactose, and maltose. As used herein, "oligosaccharide" molecules consist of about 3 to about 20 covalently linked monosaccharide units. Unless indicated otherwise herein, all references to specific sugars are intended to include the D-stereoisomer, the L-stereoisomer, and mixtures of the stereoisomers.

As used herein, the term "$C_n$ sugar" includes monosaccharides having n carbon atoms; disaccharides comprising monosaccharide units having n carbon atoms; and oligosaccharides comprising monosaccharide units having n carbon atoms. Thus, the term "$C_5$ sugar" includes pentoses, disaccharides comprising pentose units, and oligosaccharides comprising pentose units; the term "$C_6$ sugar" includes hexoses, disaccharides comprising hexose units, and oligosaccharides comprising hexose units.

As used herein, the term "$C_n$ sugar alcohol" refers to compounds produced from $C_n$ sugars by reduction of the carbonyl group to a primary or secondary hydroxyl group. Sugar alcohols having the general formula $H(HCHO)_{x+1}H$, are derived from sugars having the general formula $H(HCHO)_xHCO$. Monosaccharides and disaccharides can be used to form sugar alcohols, though the disaccharides are not fully hydrogenated. Three examples of sugar alcohols are xylitol ($C_5$), sorbitol ($C_6$), and mannitol ($C_6$).

As used herein, the abbreviation "16HD" refers to 1,6-hexanediol. The chemical structure of 1,6-hexanediol is represented by Formula (I).

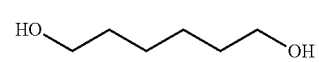

I

As used herein, the abbreviation "15PD" refers to 1,5-pentanediol. The chemical structure of 1,5-pentanediol is represented by Formula (II).

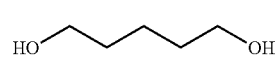

II

As used herein, the abbreviation "126HT" refers to 1,2,6-hexanetriol and includes a racemic mixture of isomers. The chemical structure of 1,2,6-hexanetriol is represented by Formula (III).

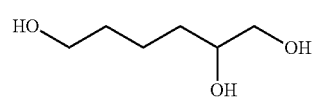

III

As used herein, the abbreviation "125PT" refers to 1,2,5-pentanetriol and includes a racemic mixture of isomers. The chemical structure of 1,2,5-pentanetriol is represented by Formula (IV).

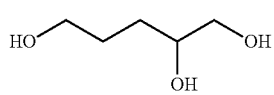

IV

As used herein, the abbreviation "Tetraol" refers to 1,2,5,6-tetrahydroxyhexane, also known as 3,4-dideoxyhexitol, and includes a mixture of stereoisomers. The chemical structure of 1,2,5,6-tetrahydroxyhexane is represented by Formula (V).

The chemical structure of hydroxymethylfurfural, also known as 5-(hydroxymethyl)-2-furaldehyde, is represented by Formula (XI).

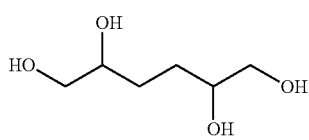

V

As used herein, the abbreviation "Pentaol" refers to 1,2,3,5,6-hexanepentaol and includes a racemic mixture of isomers. The chemical structure of 1,2,3,5,6-hexanepentaol is represented by Formula (VI).

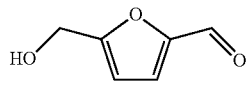

XI

The chemical structure of furfuryl alcohol, also known as 2-furanmethanol, is represented by Formula (XII).

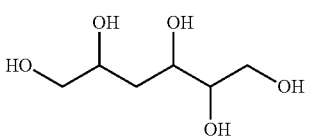

VI

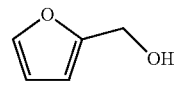

XII

As used herein, the abbreviation "THFdM" refers to tetrahydro-2,5-furandimethanol (also known as tetrahydrofuran-2,5-dimethanol or 2,5-tetrahydrofurandimethanol, or 2,5-bis[hydroxymethyl]tetrahydrofuran) and includes a mixture of stereoisomers (cis and racemic trans isomers). The chemical structure of tetrahydro-2,5-furandimethanol is represented by Formula (VII).

The chemical structure of tetrahydrofurfuryl alcohol, also known as tetrahydro-2-furanmethanol, is represented by Formula (XIII).

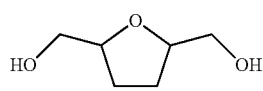

VII

XIII

The chemical structure of 2,5-dihydrofuran-2,5-dimethanol is represented by Formula (VIII).

As used herein, the abbreviation "THPM" refers to tetrahydro-2H-pyran-2-methanol, also known as 2-hydroxymethyltetrahydropyran, and includes a racemic mixture of isomers. The chemical structure of tetrahydro-2H-pyran-2-methanol is represented by Formula (XIV).

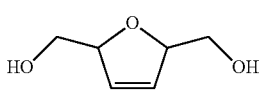

VIII

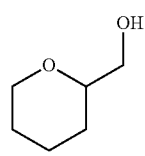

XIV

As used herein, the abbreviation "FdM" refers to 2,5-furandimethanol, also known as 2,5-bis(hydroxymethyl)furan. The chemical structure of 2,5-furandimethanol is represented by Formula (IX).

As used herein, the abbreviation "HOTHPM" refers to 2-hydroxymethyl-5-hydroxytetrahydro-2H-pyran, also known as 5-hydroxy-2H-tetrahydropyran-2 methanol or 1,5-anhydro-3,4-dideoxyhexitol, and includes a mixture of stereoisomers. The chemical structure of 2-hydroxymethyl-5-hydroxytetrahydro-2H-pyran is represented by Formula (XV).

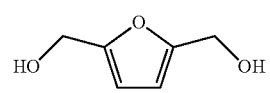

IX

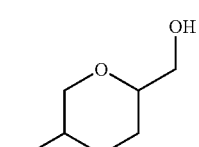

XV

The chemical structure of furfural, also known as furan-2-carbaldehyde or 2-furaldehyde, is represented by Formula (X).

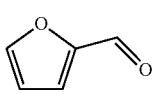

X

The chemical structure of 3,4-dihydro-2H-pyran-2-carbaldehyde, also known as 3,4-dihydro-2H-pyran-2-carboxaldehyde, 2-formyl-3,4-dihydro-2H-pyran, or "acrolein dimer", is represented by Formula (XVI).

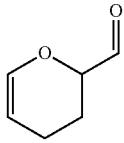

XVI

The chemical structure of levoglucosan, also known as 1,6-anhydro-β-glucopyranose, is represented by Formula (XVII).

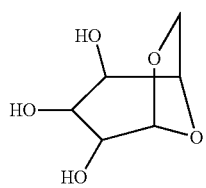

XVII

As used herein, the abbreviations "Lgone" and "LGone" refer to levoglucosenone, also known as 1,6-anhydro-3,4-dideoxy-β-D-pyranosen-2-one. The chemical structure of levoglucosenone is represented by Formula (XVIII).

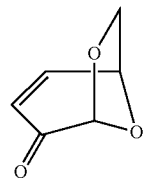

XVIII

The chemical structure of 1,6-anhydro-3,4-dideoxy-β-D-pyranose-2-one is represented by Formula (XIX).

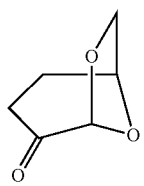

XIX

The chemical structure of levoglucosenol, also known as 1,6-anhydro-3,4-dideoxy-β-erythro-hex-3-enopyranose, is represented by Formula (XX).

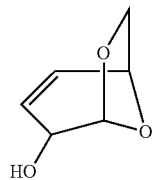

XX

As used herein, the abbreviations "Lgol" and "LGol" refer to levoglucosanol, also known as 1,6-anhydro-3,4-dideoxyhexopyranose, and include a mixture of the threo and erythro stereoisomers. The chemical structure of 1,6-anhydro-3,4-dideoxyhexopyranose is represented by Formula (XXI).

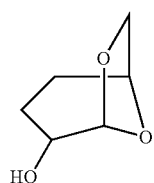

XXI

As used herein, the abbreviation "ISOS" refers to isosorbide, also known as 1,4:3,6-dianhydrosorbitol or 1,4-dianhydrosorbitol. The chemical structure of isosorbide is represented by Formula (XXII).

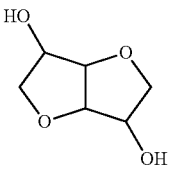

XXII

The chemical structure of sorbitol, also known as hexane-1,2,3,4,5,6-hexol, is represented by Formula (XXIII).

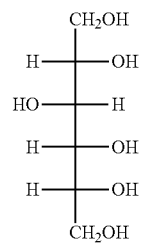

XXIII

```
         CH2OH
    H ─────── OH
    HO ─────── H
    H ─────── OH
    H ─────── OH
         CH2OH
```

The chemical structure of glucose, also known as dextrose or 2,3,4,5,6-pentahydroxyhexanal, is represented by Formula (XXIV).

XXIV

```
         CHO
    H ─────── OH
    HO ─────── H
    H ─────── OH
    H ─────── OH
         CH2OH
```

The chemical structure of fructose, also known as levulose, is represented by Formula (XXV).

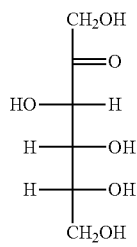

XXV

The chemical structure of xylitol, also known as pentane-1,2,3,4,5-pentol, is represented by Formula (XXVI).

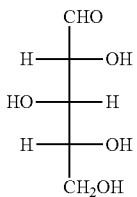

XXVI

In one embodiment, a process is provided for preparing an $\alpha,\omega$-$C_n$-diol via selective hydrodeoxygenation, the process comprising the steps:

(a) providing a feedstock comprising a $C_n$ oxygenate;

(b) contacting the feedstock with hydrogen gas, in the presence of a catalyst at a temperature and for a time sufficient to form a product mixture comprising an $\alpha,\omega$-$C_n$-diol; wherein n is 5 or greater;

and wherein the catalyst comprises Pt, Cu, Ni, Pd, Rh, Ir, Ru, or Fe on a $WO_3$ support.

In another embodiment, a process is provided for preparing an $\alpha,\omega$-$C_n$-diol via selective hydrodeoxygenation, the process comprising the steps:

(a) providing a feedstock comprising a $C_n$ oxygenate;

(b) contacting the feedstock with hydrogen gas, in the presence of a catalyst at a temperature and for a time sufficient to form a product mixture comprising an $\alpha,\omega$-$C_n$-diol; wherein n is 5 or greater;

and wherein the catalyst comprises a metal M1 and a metal M2 or an oxide of M2, and optionally a support, wherein:

M1 is Pd, Pt, or Ir; and M2 is Mo, W, V, Mn, Re, Zr, Ni, Cu, Zn, Cr, Ge, Sn, Ti, Au, or Co; or M1 is Rh and M2 is Mo, W, V, Mn, Ni, Cu, Zn, Cr, Ge, Sn, Ti, Au, or Zr; or M1 is Ag, Au or Co; and M2 is Re, Mo, or W; or M1 is Cu, Pd, Fe, or Ni; and M2 is Re, Mo, Cu, Zn, Cr, Ge, Sn, or W; or M1 is Ag, Pt, Cu, or Au, and M2 is Ni, Fe, Sn, Ge, or Ir; or M1 is Co and M2 is Fe; or M1 is Ni and M2 is Co or Fe; or M1 is Mn and M2 is Cr.

In one embodiment, n=5 or 6. In one embodiment, n=5, and the $\alpha,\omega$-$C_n$-diol is 1,5-pentanediol. In one embodiment, n=6, and the $\alpha,\omega$-$C_n$-diol is 1,6-hexanediol. In one embodiment, n=7, and the $\alpha,\omega$-$C_n$-diol is 1,7-heptanediol. In one embodiment, n=8, and the $\alpha,\omega$-$C_n$-diol is 1,8-octanediol.

Examples of $C_n$ oxygenates that are suitable for use in the present processes include 1,2,6-hexanetriol; 1,2,5-pentanetriol; 2H-tetrahydropyran-2-methanol; tetrahydrofuran-2,5-dimethanol; furan-2,5-dimethanol; 2,5 dihydrofuran-2,5-dimethanol; levoglucosenone; levoglucosan; levoglucosenol; 1,6-anhydro-3,4-dideoxy-p-D-pyranose-2-one; isosorbide; hydroxymethylfurfural; sorbitol; glucose; fructose; xylitol; 3,4-dihydro-2H-pyran-2-carbaldehyde; 1,2,5,6-hexanetetraol; 1,2,3,5,6-hexanepentanol; 1,5-anhydro-3,4-dideoxyhexitol; 5-hydroxy-2H-tetrahydropyran-2 methanol; furfural; furfuryl alcohol; tetrahydrofurfuryl alcohol; pentoses; dimers containing pentose; oligomers containing pentose; hexoses; dimers containing hexose; oligomers containing hexose; condensation products from the reaction of 5-(hydroxymethyl)-2-furfural ("HMF") with ketones and/or aldehydes, and condensation products from the reaction of furfural with ketones and/or aldehydes. The feedstock may comprise one or more Cn oxygenates.

In one embodiment, the $C_n$ oxygenate comprises 1,2,6-hexanetriol; 2H-tetrahydropyran-2-methanol; tetrahydrofuran-2,5-dimethanol; levoglucosenone; 3,4-dihydro-2H-pyran-2-carbaldehyde, or mixtures thereof. These $C_n$ oxygenates are useful for preparation of reaction mixtures comprising 1,6-hexanediol by the processes disclosed herein. In one embodiment, the $C_n$ oxygenate comprises 1,2,6-hexanetriol.

In one embodiment, the $C_n$ oxygenate comprises 1,2,5-pentanetriol; furfural; furfuryl alcohol; tetrahydrofurfuryl alcohol; xylitol; or mixtures thereof. These $C_n$ oxygenates are useful for preparation of product mixtures comprising 1,5-hexanediol by the processes disclosed herein.

Examples of suitable pentoses include without limitation xylose, arabinose, lyxose, xylitol, and ribose. Examples of suitable hexoses include without limitation glucose, mannose, fructose, and galactose. Examples of condensation products from the reaction of furfural or 5-(hydroxymethyl)-2-furfural with ketones and/or aldehydes are described in Synthesis (2008), (7), 1023-1028 (e.g., CAS Reg. No. 1040375-91-4 and CAS Reg. No. 886-77-1); and in ChemSusChem (2010), 3(10), 1158-1161, in which subjecting furfural and 5-(hydroxymethyl)-2-furfural to aldol condensation produced molecules having 8 to 15 carbon atoms.

Suitable $C_n$ oxygenates can be derived from biorenewable resources including biomass. Biomass may be derived from a single source, or biomass can comprise a mixture derived from more than one source; for example, biomass could comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste or a combination thereof. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, and animal manure or a combination thereof. Biomass that is useful for the invention may include biomass that has a relatively high carbohydrate value, is relatively dense, and/or is relatively easy to collect, transport, store and/or handle. In one embodiment, the $C_n$ oxygenate is ultimately derived from corn cobs, sugar cane bagasse, switchgrass, wheat straw, sawdust and other wood waste, and lignocellulosic feedstocks.

A biorenewable resource such as biomass can be pyrolyzed under high temperature conditions in the presence of an acid catalyst to provide useful chemical intermediates. For example, pyrolysis of wood, starch, glucose or cellulose can produce levoglucosenone by known and conventional methods (see, for example, Ponder (*Applied Biochemistry and Biotechnology*, Vol 24/25, 41-41 (1990)) or Shafizadeh (*Carbohydrate Research,* 71, 169-191 (1979)).

Glycerol can be obtained from a biorenewable resource, for example from hydrolysis of vegetable and animal fats and oils (that is, triacylglycerides comprising ester functionality resulting from the combination of glycerol with $C_{12}$ or greater fatty acids). 1,2,6-Hexanetriol can be obtained from materials such as glucose, cellulose or glycerol derived from a biorenewable resource. For example, 1,2,6-hexanetriol can be obtained by a process comprising the steps of contacting glycerol with a catalyst to prepare acrolein, heating acrolein (optionally in the presence of a catalyst) to prepare 2-formyl-3,4-dihydro-2H-pyran, contacting 2-formyl-3,4-dihydro-2H-pyran with water to prepare 2-hydroxyadipic aldehyde and contacting 2-hydroxyadipic aldehyde with hydrogen and a catalyst to produce a product mixture comprising 1,2,6-hexanetriol. See, for example, U.S. Pat. No. 2,768,213, German Patent No. 4238493, and L. Ott, et al. in *Green Chem.,* 2006, 8, 214-220.

The catalysts utilized in the processes described herein can be synthesized by any conventional method for preparing catalysts, for example, deposition of metal salts from aqueous or organic solvent solutions via impregnation or incipient wetness, precipitation of an M1 component and/or an M2 component, or solid state synthesis. Preparation may comprise drying catalyst materials under elevated temperatures from 30-250° C., preferably 50-150° C.; calcination by heating in the presence of air at temperatures from 250-800° C., preferably 300-450° C.; and reduction in the presence of hydrogen at 100-400° C., preferably 200-300° C., or reduction with alternative reducing agents such as hydrazine, formic acid or ammonium formate. The above techniques may be utilized with powdered or formed particulate catalyst materials prepared by tableting, extrusion or other techniques common for catalyst synthesis. Where powdered catalysts materials are utilized, it will be appreciated that the catalyst support or the resulting catalyst material may be sieved to a desired particle size and that the particle size may be optimized to enhance catalyst performance.

In one embodiment of the present invention, the catalyst comprises Pt, Cu, Ni, Pd, Rh, Ir, Ru, or Fe on a $WO_3$ or WOx support. The metal can be derived from any appropriate metal compound; examples include but are not limited to: rhodium (III) chloride hydrate, tetraamineplatinum (II) nitrate, ruthenium (III) chloride hydrate, copper (II) nitrate hydrate, palladium nitrate, nickel (II) chloride hexahydrate, iridium (IV) chloride hydrate, and iron (III) nitrate nonahydrate. The WOx support is considered to contain partially reduced tungsten trioxide, with the oxidation state of some of the tungsten being less than (VI) but more than (I).

The loading of M1 may be 0.1-50% but preferably 0.5-5% by weight, based on the weight of the prepared catalyst (i.e., including the $WO_3$ or $WO_x$ support). The M1/$WO_3$ catalysts can be prepared, for example, by grinding and sieving the $WO_3$ support material as desired and impregnating into the support via incipient wetness the M1-containing compound dissolved in a minimum of water, followed by drying (e.g., in vacuum at 110° C. for overnight) and then calcining in air at 300-500° C. for several (e.g., 3 to 5) hours. The M1/WOx catalyst can be prepared, for example, by adding the M1-containing compound to an aqueous solution of ammonium tungsten oxide hydrate, followed by drying the resulting solid and then calcining it in air, as described in the Experimental section.

In another embodiment, the catalyst comprises a metal M1 and a metal M2 or an oxide of M2, and optionally a support, wherein:

M1 is Pd, Pt, or Ir; and M2 is Mo, W, V, Mn, Re, Zr, Ni, Cu, Zn, Cr, Ge, Sn, Ti, Au, or Co; or M1 is Rh and M2 is Mo, W, V, Mn, Ni, Cu, Zn, Cr, Ge, Sn, Ti, Au, or Zr; or M1 is Ag, Au or Co; and M2 is Re, Mo, or W;

M1 is Cu, Pd, Fe, or Ni; and M2 is Re, Mo, Cu, Zn, Cr, Ge, Sn, or W; or

M1 is Ag, Pt, Cu, or Au, and M2 is Ni, Fe, Sn, Ge, or Ir; or

M1 is Co and M2 is Fe; or

M1 is Ni and M2 is Co or Fe; or

M1 is Mn and M2 is Cr.

In one embodiment, the catalyst comprises metals M1 and M2, and optionally a support, wherein M1 is Pd, Pt, or Ir; and M2 is Mo, W, Mn, Re, Zr, Ni, Cu, Zn, Cr, Ti, Au, or Co; or M1 is Rh and M2 is Mo, W, Mn, Ni, Cu, Zn, Cr, Ti, Au, or Zr; or M1 is Ag, Au or Co; and M2 is Re, Mo, or W; or M1 is Cu, Pd, Fe, or Ni; and M2 is Re, Mo, Cu, Zn, Cr, or W; or M1 is Ag, Pt, Cu, or Au, and M2 is Ni, Fe, or Ir.

In one embodiment, the catalyst comprises metals M1 and M2, and optionally a support, wherein M1 is Pd, Pt, or Ir; and M2 is Mo, W, V, Mn, Re, Zr, Ni, Cu, Zn, Cr, Ge, Sn, Ti, Au, or Co.

In one embodiment, the catalyst comprises metals M1 and M2, and optionally a support, wherein M1 is Cu, Pd, Fe, or Ni; and M2 is Re, Mo, Cu, Zn, Cr, Ge, Sn, or W.

In one embodiment, the catalyst comprises metals M1 and M2, and optionally a support, wherein M1 is Pt and M2 is W; or M1 is Ni and M2 is W; or M1 is Cu and M2 is W; or M1 is Cu and M2 is Fe. In one embodiment, M1 is Pt and M2 is W. In one embodiment, M1 is Ni and M2 is W. In one embodiment, M1 is Cu and M2 is W. In one embodiment, M1 is Cu and M2 is Fe.

The M1 and M2 components of the catalysts may be derived from any appropriate metal compound. Examples include but are not limited to: rhodium (III) chloride hydrate, copper (II) nitrate hydrate, nickel (II) chloride hexahydrate, iridium (IV) chloride hydrate, iron (III) nitrate nonahydrate, tetraamineplatinum (II) nitrate, platinum chloride, hexachloroplatinic acid, tetrachloroplatinic acid, palladium chloride, palladium nitrate, palladium acetate, iridium trichloride, ammonium perrhenate, ammonium tungsten oxide hydrate, ammonium molybdate hydrate, manganese (II) nitrate hydrate, and ammonium vanadium oxide.

The loading of M1 may be 0.1-50% but preferably 0.5-5% by weight, based on the weight of the prepared catalyst (i.e., including the catalyst support where present). The loading of M2 may be 0.1-99.9%, preferably 2-10%. Preferably the molar ratio of M1 to M2 in catalysts containing both M1 and M2 is in the range of 1:0.5 to 1:5. Optionally, M2 may be incorporated into the catalyst support or serve as the catalyst support, e.g. Pt supported on tungsten oxide or molybdenum oxide. Regarding the catalyst, all percentages are interpreted as weight percent relative to the weight of the prepared catalyst.

In some embodiments, it is useful to utilize a catalyst which comprises a support to enhance the stability and economic feasibility of the process. Examples of useful supports include $WO_3$, $SiO_2$, $Al_2O_3$, carbon, SiC, $TiO_2$, $ZrO_2$, $SiO_2$—$Al_2O_3$, clays such as montmorillonite, $SiO_2$—$TiO_2$, tungstated $ZrO_2$, $V_2O_5$, $MoO_3$, and zeolites such as H—Y, FAU (H—Y or USY), BEA (H-Beta), MFI (H-ZSM5), MEL (H-ZSM11) and MOR (H-Mordenite). Typically, tungstated $ZrO_2$ can comprise up to about 19 wt % Was $WO_3$ on $ZrO_2$, see for example S. Kuba et al in Journal of Catalysis 216 (2003), p. 353-361. In one embodiment, the catalyst further comprises a support comprising $WO_3$, $SiO_2$, $Al_2O_3$, carbon, $TiO_2$, $ZrO_2$, $SiO_2$—$Al_2O_3$, montmorillonite, $SiO_2$—$TiO_2$, tungstated $ZrO_2$, H—Y zeolites, $V_2O_5$, $MoO_3$, or mixtures thereof. In one embodiment, the support comprises $TiO_2$, a zeolite, or mixtures thereof. In one embodiment, the support comprises $TiO_2$, a zeolite, or mixtures thereof, and M1 is Pt and M2 is W. In other embodiments, it may be desirable to not have a support.

In some embodiments, the catalyst is mixed with an additive comprising $WO_3$, $SiO_2$, $Al_2O_3$, carbon, $TiO_2$, $ZrO_2$, $SiO_2$—$Al_2O_3$, montmorillonite, $SiO_2$—$TiO_2$, tungstated $ZrO_2$, H—Y zeolites, $V_2O_5$, $MoO_3$, or mixtures thereof. If the catalyst comprises a support, the support can be the same or different from the additive. As used herein, the term "support" means a material which is a component of the catalyst (in the cases where the optional support is present in the catalyst) and is used as part of catalyst preparation to anchor the metals M1 and M2, providing a surface for metals M1 and M2 to associate with. As used herein, the term "additive" means a material which can increase catalyst activity through its physical presence in combination with the catalyst and reactants under appropriate reaction conditions. Useful ratios of additive to catalyst are from 1:10 to 10:1 on a weight basis, for example 2:1 to 1:2, or about 1:1, although ratios outside these ranges can also be used. The additive can be added to the reactor together with the catalyst, or the catalyst and the additive may be added sequentially to the reactor. The additive, or a mixture of additive and catalyst, can be in any physical form typical for the material, including but not limited to powdered (also known as "fluidized") forms with 0.01-150 μm particle size, formed tablets, extrudates, spheres, engineered particles having uniform 0.5-10 mm size, or combinations of two or more of the above.

In some embodiments, wherein the optional support is present in the catalyst and comprises $WO_3$, $SiO_2$, $Al_2O_3$, carbon, $TiO_2$, $ZrO_2$, $SiO_2$—$Al_2O_3$, montmorillonite, $SiO_2$—$TiO_2$, tungstated $ZrO_2$, zeolites, $V_2O_5$, $MoO_3$, or mixtures thereof, the process step (b) further comprises the presence of an additive comprising $WO_3$, $SiO_2$, $Al_2O_3$, carbon, $TiO_2$, $ZrO_2$, $SiO_2$—$Al_2O_3$, montmorillonite, $SiO_2$—$TiO_2$, tungstated $ZrO_2$, zeolites, $V_2O_5$, $MoO_3$, or mixtures thereof. In some embodiments, the optional support is present in the catalyst and step (b) further comprises adding an additive comprising $WO_3$, $SiO_2$, $Al_2O_3$, carbon, $TiO_2$, $ZrO_2$, $SiO_2$—$Al_2O_3$, montmorillonite, $SiO_2$—$TiO_2$, tungstated $ZrO_2$, zeolites, $V_2O_5$, $MoO_3$, or mixtures thereof. Process step (b) refers to contacting the feedstock with hydrogen gas, in the presence of a catalyst at a temperature and for a time sufficient to form a product mixture comprising an $\alpha,\omega$-$C_n$-diol, wherein n is 5 or greater, and wherein the catalyst is as disclosed herein. In some embodiments, the additive comprises $TiO_2$. In some embodiments, the additive comprises $SiO_2$. In some embodiments, the additive comprises $ZrO_2$. In some embodiments, the additive comprises $Al_2O_3$. In some embodiments, the additive comprises $MoO_3$. In some embodiments, the additive comprises carbon.

In some embodiments, the process for preparing an $\alpha,\omega$-$C_n$-diol comprises the steps:

(a) providing a feedstock comprising a $C_n$ oxygenate;

(b) contacting the feedstock with hydrogen gas, in the presence of a catalyst, and optionally an additive, at a temperature and for a time sufficient to form a product mixture comprising an $\alpha,\omega$-$C_n$-diol; wherein n is 5 or greater;

and wherein the catalyst comprises a metal M1 and a metal M2 or an oxide of M2, and optionally a support, wherein:

M1 is Pd, Pt, or Ir; and M2 is Mo, W, V, Mn, Re, Zr, Ni, Cu, Zn, Cr, Ge, Sn, Ti, Au, or Co; or M1 is Rh and M2 is Mo, W, V, Mn, Ni, Cu, Zn, Cr, Ge, Sn, Ti, Au, or Zr; or M1 is Ag, Au or Co; and M2 is Re, Mo, or W; or M1 is Cu, Pd, Fe, or Ni; and M2 is Re, Mo, Cu, Zn, Cr, Ge, Sn, or W; or M1 is Ag, Pt, Cu, or Au, and M2 is Ni, Fe, Sn, Ge, or Ir; or M1 is Co and M2 is Fe; or M1 is Ni and M2 is Co or Fe; or M1 is Mn and M2 is Cr; and wherein the additive comprises $WO_3$, $SiO_2$, $Al_2O_3$, carbon, $TiO_2$, $ZrO_2$, $SiO_2$—$Al_2O_3$, montmorillonite, $SiO_2$—$TiO_2$, tungstated $ZrO_2$, zeolites, $V_2O_5$, $MoO_3$, or mixtures thereof.

The prepared catalyst can be in any physical form typical for heterogeneous catalysts, including but not limited to: powdered (also known as "fluidized") forms with 0.01-150 μm particle size, formed tablets, extrudates, spheres, engineered particles having uniform 0.5-10 mm size, monolithic structures on which surfaces the catalyst is applied, or combinations of two or more of the above. When a solid support is utilized a catalyst containing both M1 and M2, it is desirable that M1 be intimately associated with the M2 component, as measured by transmission electron microscopy with energy dispersive spectroscopy. It is further preferable that the particle size of the M1 component be less than 10 nm and most preferably less than 3 nm as measured by the same techniques. In this case, particle size of the M1 component may be interpreted as particle size of a mixture of the M1 and M2 components, an alloy of the M1 and M2 components, a particle of the M1 component adjacent to a particle of the M2 component, or a particle of the M1 component on the support which contains the M2 component.

The catalyst may be present in any weight ratio to the feedstock sufficient to catalyze the hydrodeoxygenation, generally in the range of 0.0001:1 to 1:1, preferably 0.001:1 to 0.5:1 for batch reactions. For continuous reactions, the same ratios are appropriate where the weight ratio of feed to catalyst is defined as weight of $C_n$ oxygenate feed processed per weight of catalyst.

Useful temperatures for the processes are between about 30° C. and about 300° C. In some embodiments, the temperature is between and optionally includes any two of the following values: 30° C., 40° C., 50° C., 60° C., 70° C., 80° C., 90° C., 100° C., 110° C., 120° C., 130° C., 140° C., 150° C., 160° C., 170° C., 180° C., 190° C., 200° C., 210° C., 220° C., 230° C., 240° C., 250° C., 260° C., 270° C., 280° C., 290° C., and 300° C. It is expected that with some catalysts, temperatures above about 300° C. could be used.

The process is conducted by contacting a Cn oxygenate feed with hydrogen in the presence of the catalyst for a time sufficient to form a product mixture comprising an $\alpha,\omega$-$C_n$-diol. The mole ratio of hydrogen to feed is not critical as long as sufficient hydrogen is present to produce the desired $\alpha,\omega$-$C_n$-diol. Hydrogen is preferably used in excess, and may optionally be used in combination with an inert gas such as nitrogen or argon. If an inert gas is used in combination with the hydrogen, the amount of the inert gas should be such that it does not negatively impact the formation of the product mixture. The pressure of the process may be between about 300 kPa and about 25,000 kPa, for example between 5000 and 150,000 kPa. In some embodiments, the pressure of the process is between and optionally includes any two of the following values: 300; 500; 1000; 1500; 2000; 2500; 3000; 3500; 4000; 4500; 5000; 10,000; 15,000; 20,000; and 25,000 kPa.

The process is typically conducted in the presence of a solvent, which may serve to reduce the viscosity of the system to improve fluidity of the catalyst in the reaction vessel and/or to remove the heat of reaction and improve the performance of the process. Polar solvents are preferred. The solvent may be present in a range of 1% to 95% by weight of the total reaction mixture, excluding the catalyst.

The reaction products may be isolated or purified by any common methods known in the art including but not limited to distillation, wiped film evaporation, chromatography, adsorption, crystallization, and membrane separation.

It will be appreciated that the processes disclosed herein can also be utilized to prepare useful intermediates or byproducts in the synthesis of the α,ω-diols through optimization of the process parameters. Examples of intermediates that can be prepared during synthesis of 1,5-pentanediol and/or 1,6-hexanediol include but are not limited to furan dimethanol: tetrahydrofuran dimethanol; tetrahydropyran-2-methanol; levoglucosanol; and furfuryl alcohol. Examples of byproducts which can be obtained during synthesis of 1,5-pentanediol and/or 1,6-hexanediol include but are not limited to isomeric hexanols; isomeric pentanols; 1,5-hexanediol; 1,2-hexanediol; 2-methyltetrahydropyran; 2,5-dimethyltetrahydrofuran; 1,2-cyclohexanediol; 1,2-cyclopentanediol; cyclohexanol, and mixtures thereof.

The α,ω-$C_n$-diols obtained by the processes disclosed herein can be converted to industrially useful materials such as α,ω-$C_n$-diaminoalkanes. For example, 1,5-pentanediol and 1,6-hexanediol can be reductively aminated to 1,5-pentanediamine (1,5-diaminopentane) and 1,6-hexanediamine (1,6-diaminohexane), respectively, by methods known in the art. See, for example, U.S. Pat. No. 3,215,742; U.S. Pat. No. 3,268,588; and U.S. Pat. No. 3,270,059.

In some embodiments, the processes disclosed herein further comprise the steps:

(c) optionally, isolating the α,ω-$C_n$-diol from the product mixture;

(d) contacting the α,ω-$C_n$-diol with ammonia and hydrogen in the presence of a reductive amination catalyst at a temperature and for a time sufficient to form a second product mixture comprising an α,ω-$C_n$ diaminoalkane; and (e) optionally, isolating the α,ω-$C_n$-diaminoalkane from the second product mixture.

In one embodiment, the α,ω-$C_n$-diaminoalkane comprises 1,6-diaminohexane. In one embodiment, the α,ω-$C_n$-diaminoalkane comprises 1,5-diaminopentane.

The reductive amination catalyst contains at least one element selected from Groups IB, VIB, VIIB, and VIII of the Periodic Table, for example iron, cobalt, nickel, ruthenium, rhodium, palladium, osmium, copper, chromium, iridium, or platinum. The elements may be in the zero oxidation state or in the form of a chemical compound. The reductive amination catalyst may be supported, unsupported or Raney-type. In one embodiment, the reductive amination catalyst contains ruthenium. In one embodiment, the reductive amination catalyst contains nickel. In one embodiment, the reductive amination catalyst is Raney nickel. In one embodiment, the reductive amination catalyst is Raney copper. In one embodiment, the reductive amination catalyst is Raney cobalt.

The reductive amination step is conducted by contacting the α,ω-$C_n$-diol, or a product mixture comprising the α,ω-$C_n$-diol, with ammonia and hydrogen in the presence of the catalyst for a time sufficient to form a second product mixture comprising an α,ω-$C_n$-diaminoalkane. Useful temperatures for the reductive amination step are in the range of about 40° C. to 300° C., for example in the range of about 75° C. to 150° C. Typically pressures are in the range of about 2 MPa to 35 MPa, for example in the range of about 4 MPa to 12 MPa. The molar ratio of hydrogen to the α,ω-$C_n$-diol is typically equal to or greater than 1:1, for example in the range of 1:1 to 100:1, or in the range of 1:1 to 50:1.

The reductive amination step is typically performed in liquid ammonia solvent. The ammonia is used in stoichiometric excess with reference to the α,ω-$C_n$-diol. Typically, a molar ratio of 1:1 to 80:1 of ammonia to the α,ω-$C_n$-diol can be used, for example a molar ratio in the range of 10:1 to 50:1. Optionally, an additional solvent such as water, methanol, ethanol, butanol, pentanol, hexanol, an, ester, a hydrocarbon, tetrahydrofuran, or dioxane, can be used. The weight ratio of the additional solvent to the α,ω-$C_n$-diol is typically in the range of 0.1:1 to 5:1.

The reductive amination step can be performed in a fixed bed reactor or in a slurry reactor, for example a batch, continuous stirred tank reactor or bubble column reactor. The α,ω-$C_n$-diamine may be isolated from the second product mixture by any common methods known in the art, for example fractional distillation under moderate vacuum.

EXAMPLES

The processes described herein are illustrated in the following examples. From the above discussion and these examples, one skilled in the art can ascertain the essential characteristics of this invention, and without departing from the spirit and scope thereof, can make various changes and modifications to adapt it to various uses and conditions.

The following abbreviations are used in the examples: "° C." means degrees Celsius; "wt %" means weight percent; "g" means gram(s); "min" means minute(s); "h" means hour(s); "µL" means microliter(s); "wt %" means weight percent; "RV(s)" means reaction vessel(s); "psi" means pounds per square inch; "mg/g" means milligram(s) per gram; "µm" means micrometer(s); "mL" means milliliter(s); "mm" means millimeter(s); "cm" means centimeter(s); "mL/min" means milliliter(s) per minute; "kPa" means kilopascal; "MPa" means megapascal(s); "$m^2/g$" means square meters per gram; "GC" means gas chromatography; "MS" means "mass spectrometry"; "Conv" means conversion; "sel" means selectivity; "LHSV" means liquid hourly space velocity; "GTO" means gas to oil ratio; "12HD" means 1,2-hexanediol; "12CHD" means 1,2-cyclohexanediol; "c12CHD" means cis-1,2-cyclohexanediol; "1H" means 1-hexanol; "1P" means 1-pentanol; "15HD" means 1,5-hexanediol.

Materials

All commercial materials were used as received unless stated otherwise. 1,2,6-hexanetriol (>=97 GC area % purity) was obtained from Evonik DEGUSSA GmBH, Marl, Germany. Tetrahydrofuran-2,5-dimethanol (97% purity) was obtained from Aldrich. 2-Hydroxymethyltetrahydropyran (98% purity) was obtained from Aldrich. N-Hexanol (98% purity) was obtained from Aldrich. Deionized water (DI) (pH=5.2) was used unless otherwise indicated. Commercially available metal salts used in catalyst preparation are listed in Table 1. Catalyst supports and zeolites used for catalyst preparation are described in Tables 2 and 3.

TABLE 1

Commercially Available Metal Salts Used in Catalyst Preparation

| Metal Salt | Source |
| --- | --- |
| Rhodium (III) Chloride Hydrate | Strem |
| Tetraammineplatinum (II) Nitrate | Aldrich |
| Ruthenium (III) Chloride Hydrate | Alfa Aesar |
| Copper (II) Nitrate Hydrate | Alfa Aesar |
| Palladium Nitrate | Alfa Aesar |
| Nickel (II) nitrate Hexahydrate | Aldrich |
| Iridium (IV) Chloride Hydrate | Aldrich |
| Tin (II) Chloride Dihydrate | Aldrich |
| Hydrogen Tetrachloroaurate (III) Trihydrate | Aldrich |
| Silver Nitrate | Aldrich |
| Iron (III) Nitrate Nonahydrate | Aldrich |
| Cobalt (II) Nitrate Hexahydrate | Aldrich |
| Ammonium Perhenate | Aldrich |
| Ammonium Tungsten Oxide Hydrate | Alfa Aesar |
| Ammonium Molybdate Hydrate | Alfa Aesar |
| Manganese (II) Nitrate Hydrate | Alfa Aesar |
| Ammonium Vanadium Oxide | Alfa Aesar |
| Zirconium Dinitrate Oxide Hydrate | Alfa Aesar |
| Chromium (III) Nitrate Nonahydrate | Aldrich |

TABLE 2

Supports Used in Catalyst Syntheses and Their Commercial Sources

| Material | Vendor | Identifier |
| --- | --- | --- |
| $SiO_2$ | EMD | Silica Gel 60 |
| $Al_2O_3$ | J. T. Baker | |
| Celite ® 545 | EMD | Celite ®545 |
| $TiO_2$ | Evonik Industries | Aerolyst-7708 |
| $TiO_2$ | Evonik Industries | Aerolyst-7711 |
| MgO | Spectrum | |
| Cerium(IV)Oxide | Alfa Aesar | |
| Niobium (II) Oxide | Alfa Aesar | |
| $WO_3$ | Aldrich | |
| $ZrO_2$ | Saint-Gobain | NorPro SZ31107 |

For catalysts comprising a $TiO_2$ support, the $TiO_2$ was Aerolyst-7708 from Evonik Industries unless otherwise indicated.

TABLE 3

Commercially Available Zeolites Used in Catalyst Syntheses and Their Commercial Sources

| Material Identifier | Description | Vendor | Composition/Characteristics |
| --- | --- | --- | --- |
| Silica-Alumina | | Aldrich | |
| Zeolyst CP814E | Zeolite-Beta | Zeolyst | $SiO_2/Al_2O_3$ Mole Ratio: 25<br>Nominal Cation Form: Ammonium<br>$Na_2O$ Weight %: 0.05<br>Surface Area, $m^2/g$: 680 |
| Zeolyst CBV 3024E | ZSM-5 type | Zeolyst | $SiO_2/Al_2O_3$ Mole Ratio: 30<br>Nominal Cation Form: Ammonium<br>$Na_2O$ Weight %: 0.05<br>Surface Area, $m^2/g$: 400 |
| Zeolyst CP811C-300-H-Beta MR 350 | Zeolite Beta | Zeolyst | $SiO_2/Al_2O_3$ Mole Ratio: 360<br>Nominal Cation Form: Hydrogen<br>Na2O Weight %: 0.05<br>Surface Area, $m^2/g$: 620 |
| H—Y 120/20 | Zeolite H—Y | Degussa | $SiO_2/Al_2O_3$ = 129 |
| Zeocat ZSM-5 PZ-2/50H | ZSM-5 | Chemie Uetikon | |
| LSX | LSX | Zeochem | Purmol LSX Zeolite Powder Molecular Sieve; $mNaO•mAl_2O_3•ySiO_2•xH_2O$ |
| $NH_4$ Mordenite CBV-20A | Mordenite | | |
| CBV 30011G ZSM-5 | ZSM-5 | Zeolyst | |
| PZ-2/50 H ZSM-5 | ZSM-5 | Chemie Uetikon | |
| CBV 720 | Zeolite Y | Zeolyst | $SiO_2/Al_2O_3$ Mole Ratio: 30<br>Nominal Cation Form: Hydrogen<br>Na2O Weight %: 0.03<br>Unit Cell Size, A: 24.28<br>Surface Area, $m^2/g$: 780 |
| CBV 2802 | H-ZSM-5 | Zeolyst | |
| PZ-2/50 H | H-ZSM-5 | Chemie Uetikon | |
| CBV 780 | Zeolite Y | Zeolyst | $SiO_2/Al_2O_3$ Mole Ratio: 80<br>Nominal Cation Form: Hydrogen<br>Na2O Weight %: 0.03<br>Unit Cell Size, A: 24.24<br>Surface Area, $m^2/g$: 780 |
| PZ-2/300 H | H-ZSM-5 | Chemie Uetikon | |
| PZ-2/250 H | H-ZSM-5 | Chemie Uetikon | |
| CBV 901 | Zeolite Y | Zeolyst | $SiO_2/Al_2O_3$ Mole Ratio: 80<br>Nominal Cation Form: Hydrogen<br>Na2O Weight %: 0.03<br>Unit Cell Size, A: 24.24<br>Surface Area, $m^2/g$: 700 |
| CBV 90A | H-mordenite | Zeolyst | |
| CBV 20A | NH4-Mordenite | PQ | |

The mixed support $TiO_2$-CBV780 was prepared as follows: 0.46 g of Aerolyst 7708 $TiO_2$ (Evonik) and 0.46 g of Zeolyst CBV780 (Zeolyst Int) that had been ground and passed through a 0.0165" mesh sieve were thoroughly mixed together with a mortar and pestle.

Analytical Methods

Reactor feed solutions and reaction product solutions were analyzed by gas chromatography using standard GC and GC/MS equipment: Agilent 5975C, HP5890, Stabilwax Column Restek Company Bellefonte, Pa. (30 m×0.25 mm, 0.5 micron film thickness). Chemical components of reaction product mixtures were identified by matching their retention times and mass spectra to those of authentic samples.

Product mixture distribution, percent conversion, percent selectivity, and % yield are defined as follows:

Product Mixture Distribution =

$$\frac{\text{Area \% of Compound}}{\text{Sum of Area \% of all observed compounds}}$$

where area percents were determined from gas chromatographic analysis.

$$\% \text{ Conversion} = \frac{100 * (\text{mol starting material charged} - \text{mol starting material remaining})}{\text{mol starting material charged}}$$

$$\% \text{ Selectivity} = \frac{100 * \text{mol of product compound}}{(\text{mol starting material charged} - \text{mol starting material remaining})}$$

$$\% \text{ Yield} = \frac{100 * \text{mol product compound}}{\text{Mol starting material charged}}$$

where mol of compounds were determined from calibrated GC methods.

In referring to $M1/WO_3$ catalysts, M1% means the weight percent of M1 based on the prepared catalyst weight. For example, 4% $Pt/WO_3$ means 0.04 g of Pt and 0.96 g of $WO_3$ in 1 g of catalyst.

In referring to $M1/WO_x$ catalysts, M1:W means the molar ratio of M1 to W based on the weight of prepared catalyst $M1/WO_x$. For example, 1:05 $Pt/WO_x$ means in any given weight of the catalyst the atomic molar ratio of Pt to W is 1:0.5.

In referring to M1M2/support catalysts, M1% means the weight percent of M1 based on the prepared catalyst weight, and M1/M2 is the molar ratio of M1 to M2 unless otherwise noted. For example, 4% $PtW/TiO_2$ (Pt/W=1) means one gram of catalyst contains 0.04 g of Pt and has a Pt/W molar ratio of 1.

In referring to $PtW/TiO_2$ (x % Pt y % W) catalysts, x % and y % represent the weight percentages of Pt and W, respectively. For example $PtW/TiO_2$ (1% Pt, 4% W) means one gram of catalyst contains 0.01 g of Pt and 0.04 g of W.

For all the catalyst syntheses, only one metal salt was used as the precursor for each metal in the catalyst; the metal salts are given in Table 1.

Preparation of $M1/WO_3$ Catalysts

A $Pt/WO_3$ catalyst containing 4 wt % Pt was synthesized as follows. 0.48 Grams of $WO_3$ support that had been ground with a mortar and pestle and passed through a 420 micron mesh sieve was placed into a glass vial. Tetraamineplatinum (II) nitrate (0.039 g) dissolved in 0.5 mL of water was then added to the $WO_3$ to impregnate Pt onto the solid support via incipient wetness. The mixture was stirred for 15 minutes, then dried overnight under vacuum at 110° C. After cooling to room temperature, the solid was calcined in air at 400° C. for 4 hours.

Other $M1/WO_3$ catalysts were prepared according to the above procedure using the appropriate amounts of corresponding M1-containing metal salts listed in Table 1. $M1/WO_3$ catalysts were used in Examples 1-11.

Examples 1-11

Hydrodeoxygenation of 1,2,6-Hexanetriol to 1,6-Hexanediol Using $M1/WO_3$ Catalysts in Batch Mode (without Pre-Reduction of the Catalyst)

In each of Examples 1-11, the conversion of 1,2,6-hexanetriol (126HT) to a reaction mixture comprising 1,6-hexanediol (16HD) was performed according to the following procedure. Approximately 1 g of an aqueous solution of 126HT (5 weight percent) and approximately 50 mg of the $M1/WO_3$ catalyst indicated in Table 1 were placed into a 1.5 mL pressure vessel containing a stir bar. The vessel was charged with $H_2$ to 1000 psig $H_2$ and heated to the reaction temperature shown in Table 4. The reaction pressure and temperature were maintained for 4 hours. The vessel was then cooled to room temperature. The reaction mixture was filtered and the reaction solution analyzed using GC methods calibrated with internal standards. Results are presented in Table 4.

TABLE 4

Conversion of 126HT to 16HD Using $M1/WO_3$ Catalysts at 1000 psig $H_2$

| Example | Temp (° C.) | Catalyst $M1/WO_3$ | M1 wt % | % Conversion | % Yield of 16HD |
|---|---|---|---|---|---|
| 1 | 180 | $Pt/WO_3$ | 2 | 65.3 | 46.4 |
| 2 | 180 | $Pd/WO_3$ | 0.5 | 7.5 | 2.1 |
| 3 | 250 | $Fe/WO_3$ | 4 | 29.7 | 6.4 |
| 4 | 250 | $Ni/WO_3$ | 4 | 23.4 | 2.4 |
| 5 | 250 | $Cu/WO_3$ | 10 | 100.0 | 37.4 |
| 6 | 250 | $Ni/WO_3$ | 10 | 100.0 | 5.0 |
| 7 | 160 | $Rh/WO_3$ | 2 | 116 | 50.4 |
| 8 | 160 | $Ir/WO_3$ | 4 | 115 | 14.3 |
| 9 | 250 | $Ru/WO_3$ | 1 | 99 | 56.3 |
| 10 | 250 | $Ag/WO_3$ | 1 | 96 | 39.9 |
| 11 | 250 | $Au/WO_3$ | 4 | 98 | 43.9 |

Preparation of $M1WO_x$ Catalysts

A $PtWO_x$ (Pt:W=0.04:1) catalyst was synthesized as follows. Ammonium tungsten oxide hydrate, $(NH_4)_{10}W_{12}O_{41}.5H_2O$, (0.680 g) was dissolved in 40.0 mL of water. To this was added a solution of tetraamineplatinum (II) nitrate (0.0396 g dissolved in 0.5 mL of water). A white solid precipitated immediately upon the addition. The slurry was mixed on a rotary evaporator for 30 minutes, and then placed into a vacuum oven and dried at 110° C. overnight. After cooling to room temperature, the material was transferred to a ceramic boat and calcined in air at 400° C. for three hours.

Other $M1WO_x$ catalysts were prepared according to the above procedure using the appropriate amounts of M1-containing metal salt and $(NH_4)_6H_2W_{12}O_{41}.5H_2O$ to attain the desired M1:W molar ratios. $M1/WO_x$ catalysts were used in Examples 12-16.

Examples 12-16

Hydrodeoxygenation of 126HT to 16HD Using $M1/WO_x$ Catalysts

Examples 12-16 were performed following the procedure of Examples 1-11 except using the $M1/WO_x$ catalysts and temperatures indicated in Table 5. Results are presented in Table 5.

TABLE 5

Conversion of 126HT to 16HD Using M1/WO$_x$ Catalysts at 1000 psig H$_2$

| Example | Temp (° C.) | Catalyst M1/WO$_x$ | M1:W molar ratio | % Conversion | % Yield of 16HD |
|---|---|---|---|---|---|
| 12 | 140 | Pt/WO$_x$ | Pt:W = 1:1 | 85.0 | 71.5 |
| 13 | 250 | Fe/WO$_x$ | Fe:W = 0.5:1 | 100.0 | 7.5 |
| 14 | 250 | Pd/WO$_x$ | Pd:W = 0.5:1 | 100.0 | 9.4 |
| 15 | 250 | Cu/WO$_x$ | Cu:W = 0.5:1 | 100.0 | 20.5 |
| 16 | 250 | Ni/WO$_x$ | Ni:W = 1:1 | 100.0 | 1.5 |

Preparation of M1M2/Support Catalysts—Catalyst Preparation Method A

A PtW/TiO$_2$ catalyst containing 4 wt % Pt and having a molar ratio of Pt:W of 1:1 was prepared according to the following procedure.

An aqueous solution of tetraamineplatinum (II) nitrate (0.079 g dissolved in 1.0 mL of water) was added to 0.92 g of TiO$_2$ (Aerolyst 7708) that had been ground with a mortar and pestle, passed through a 400 micron mesh sieve, and then wetted with water (1.0 mL). The resulting slurry was stirred at room temperature for 15 minutes, then dried overnight in a vacuum oven at 110° C. The solid material was allowed to cool to room temperature, and then wetted with 1.0 mL of water. To this was added 0.0535 g of ammonium tungsten oxide hydrate dissolved in 3.0 mL of water. The mixture was stirred for 15 minutes at room temperature, then dried overnight in a vacuum oven at 110° C. After cooling to room temperature, the material was transferred to a ceramic boat and calcined in air at 400° C. for three hours.

Other M1M2/support catalysts were prepared following the above procedure but using appropriate amounts of M1- and M2-containing metal salts from Table 1 and a selected support from Table 2 or Table 3. The catalysts prepared according to this method were used in batch mode hydrodeoxygenation Examples described below.

Examples 17-54

Hydrodeoxygenation of 126HT to 16HD Using M1M2/Support Catalysts

Examples 17-54 were performed following the procedure of Examples 1-11 except using the M1M2/support catalysts, temperatures, and reaction pressures indicated in Table 6. Results are presented in Table 6.

TABLE 6

Conversion of 126HT to 16HD Using M1M2/Support Catalysts

| Ex | Temp (° C.) | P (psig) | Catalyst (M1M2/support)* | M1 wt % | M1/M2 molar ratio | % Conv | % Yield 16HD |
|---|---|---|---|---|---|---|---|
| 17 | 250 | 1500 | CuW/TiO$_2$ | 4 | 2 | 100.0 | 35.9 |
| 18 | 250 | 1500 | CuNi/TiO$_2$ | 3 | 1 | 99.2 | 26.9 |
| 19 | 250 | 1000 | CuZn/TiO$_2$ | 10 | 2 | 6.1 | 2.7 |
| 20 | 250 | 1000 | CuCr/TiO$_2$ | 4 | 1 | 35.4 | 2.4 |
| 21 | 250 | 1000 | FeCr/CBV780 | 4 | 12 | 32.3 | 1.3 |
| 22 | 250 | 1000 | FeCr/TiO$_2$ | 4 | 1 | 18.7 | 0.6 |
| 23 | 250 | 1000 | FeZn/TiO$_2$ | 10 | 2 | 4.0 | 0.6 |
| 24 | 250 | 1000 | NiW/TiO$_2$ | 4 | 1 | 71.4 | 35.8 |
| 25 | 250 | 1000 | NiCr/CBV780 | 4 | 12 | 84.0 | 7.3 |
| 26 | 250 | 1000 | NiZn/TiO$_2$ | 10 | 2 | 47.7 | 4.6 |
| 27 | 250 | 1000 | NiCr/TiO$_2$ | 4 | 12 | 100.0 | 4.2 |
| 28 | 250 | 1000 | PdReTiO$_2$ | 4 | 1 | 93.3 | 41.5 |
| 29 | 260 | 1000 | PdW/TiO$_2$ | 4 | 1 | 41.6 | 23.3 |
| 30 | 250 | 1500 | PdMo/TiO$_2$ | 4 | 1 | 41.7 | 19.8 |
| 31 | 250 | 1000 | PdCr/CBV780 | 4 | 12 | 1.3 | 19.3 |
| 32 | 250 | 1500 | PdMo/H—Y | 4 | 1 | 6.0 | 18.8 |
| 33 | 180 | 1040 | PdMo/H—Y | 4 | 1 | 37.2 | 9.5 |
| 34 | 250 | 1000 | PdCr/TiO$_2$ | 4 | 12 | 100.0 | 3.7 |
| 35 | 250 | 1000 | PdZn/TiO$_2$ | 10 | 2 | 100.0 | 0.9 |
| 36 | 250 | 1000 | RuCu/CBV780 | 4 | 1 | 100.0 | 14.0 |
| 37 | 200 | 1000 | RuCu/TiO$_2$ | 4 | 1 | 37.4 | 17.8 |
| 38 | 200 | 1000 | RuPd/CBV780 | 4 | 1 | 100.0 | 0.3 |
| 39 | 200 | 1000 | RuFe/CBV780 | 4 | 1 | 11.4 | 0.4 |
| 40 | 200 | 1000 | RuCu/CBV780 | 4 | 1 | 100.0 | 10.3 |
| 41 | 250 | 1500 | PtMn/H—Y | 4 | 1 | 100.0 | 36.8 |
| 42 | 250 | 1100 | PtCo/CBV780 | 4 | 2 | 100.0 | 17.0 |
| 43 | 180 | 1000 | PtZr/CBV780 | 4 | 2 | 100.0 | 14.0 |
| 44 | 140 | 1000 | PtCr/TiO$_2$ | 4 | 1 | 4.9 | 1.3 |
| 45 | 250 | 1500 | PtCo/TiO$_2$ | 4 | 1 | 100.0 | 1.3 |
| 46 | 250 | 1500 | PtCo/H—Y | 4 | 1 | 65.7 | 1.1 |
| 47 | 140 | 1000 | PtCr/CBV780 | 4 | 1 | 13.3 | 0.5 |
| 48 | 140 | 1000 | PtCr/SiO$_2$ | 4 | 1 | 8.6 | 0.1 |
| 49 | 250 | 1500 | AgW/TiO$_2$ | 4 | 1 | 9.4 | 29.1 |
| 50 | 200 | 1000 | AgRe/TiO$_2$ | 4 | 1 | 12.2 | 25.9 |
| 51 | 250 | 1600 | AgRe/SiO$_2$ | 4 | 1 | 50.9 | 23.6 |
| 52 | 250 | 1600 | AgRe/H—Y | 4 | 1 | 100.0 | 22.6 |
| 53 | 250 | 1600 | AgRe/Al$_2$O$_3$ | 4 | 1 | 42.2 | 18.0 |
| 54 | 180 | 1000 | AgMo/TiO$_2$ | 4 | 1 | 99.4 | 3.2 |

*For the catalysts comprising a TiO$_2$ support, the TiO$_2$ was Aerolyst-7708 from Evonik Industries.

Examples 56-64

Hydrodeoxygenation of THPM to 16HD Using M1M2/Support Catalysts

Examples 56-64 were performed following the procedure of Examples 1-11 except using an aqueous solution of 5 wt % 2-hydroxymethyltetrahydropyran (THPM) as the substrate, the M1M2/support catalysts, and temperatures indicated in Table 7. Results are presented in Table 7.

TABLE 7

Conversion of THPM to 16HD Using M1M2/Support Catalysts at 1000 psig H$_2$.

| Ex | Temp (° C.) | Catalyst * (M1M2/Support) | M1 | M1 wt % | M1/M2 molar ratio | % Conversion | % Yield of 16HD |
|---|---|---|---|---|---|---|---|
| 56 | 250 | AgNi/CBV780 | Ag | 4 | 1 | 50.0 | 16.2 |
| 57 | 250 | AgNi/Al$_2$O$_3$ | Ag | 4 | 1 | 22.2 | 10.4 |
| 58 | 250 | AuNi/CBV780 | Au | 4 | 1 | 17.3 | 7.4 |
| 59 | 250 | CuNi/CBV780 | Cu | 4 | 1 | 25.3 | 7.3 |
| 60 | 250 | CuNi/TiO$_2$ | Cu | 4 | 1 | 19.4 | 4.7 |
| 61 | 250 | CuW/Al$_2$O$_3$ | Cu | 4 | 1 | 9.0 | 4.7 |

TABLE 7-continued

Conversion of THPM to 16HD Using M1M2/Support Catalysts at 1000 psig $H_2$.

| Ex | Temp (° C.) | Catalyst * (M1M2/ Support) | M1 | M1 wt % | M1/M2 molar ratio | % Conversion | % Yield of 16HD |
|---|---|---|---|---|---|---|---|
| 62 | 250 | CuNi/TiO$_2$ | Cu | 4 | 1 | 20.3 | 2.9 |
| 63 | 250 | PtFe/SiO$_2$ | Pt | 4 | 1 | 22.8 | 1.6 |
| 64 | 250 | PtFe/Al$_2$O$_3$ | Pt | 4 | 1 | 5.1 | 1.2 |

* For catalysts containing TiO$_2$, the TiO$_2$ supports were Aerolyst-7708 except where indicated otherwise.

Examples 65-70

Hydrodeoxygenation of 126HT to 16HD Using M1M2/Support Catalysts

Examples 65-77 were performed following the procedure of Examples 1-11 except using 2.5 wt % 126HT as the substrate, the temperatures, and the M1M2/support catalysts indicated in Table 8. Results are presented in Table 8.

TABLE 8

Conversion of 126HT to 16HD Using M1M2/Support Catalysts

| Ex | Temp (° C.) | Catalyst * (M1M2/ Support) | M1 | M2 | M1 wt % | M1/M2 molar ratio | % Conv | % Sel to 16HD |
|---|---|---|---|---|---|---|---|---|
| 65 | 220 | AgNi/TiO$_2$ | Ag | Ni | 4 | 1 | 83 | 53 |
| 66 | 220 | PtFe/TiO$_2$ | Pt | Fe | 4 | 1 | 53 | 39 |
| 67 | 250 | CuFe/TiO$_2$ | Cu | Fe | 4 | 1 | 37 | 56 |
| 68 | 250 | AuNi/TiO$_2$ | Au | Ni | 4 | 1 | 50 | 51 |
| 69 | 250 | AuIr/TiO$_2$ | Au | Ir | 4 | 1 | 33 | 25 |
| 70 | 250 | IrW/TiO$_2$ | Ir | W | 4 | 1 | 76 | 32 |

* For these Examples, the TiO$_2$ supports were Aerolyst-7711 except for the catalyst of Example 70, which contained Aerolyst-7708 TiO$_2$.

Preparation of PtW/TiO$_2$ Catalysts Containing (x % Pt, % W)—Catalyst Preparation Method B A PtW/TiO$_2$ catalyst containing 4 wt % Pt and 4 wt % W was prepared as follows. Ammonium tungsten oxide hydrate (0.170 g) dissolved in 9.5 mL of water was added to 2.88 g of TiO$_2$ (Aerolyst-7708 from Evonik Industries) that had been previously wetted with 2.8 mL of water. The mixture was stirred for 15 minutes and then excess water was removed under reduced pressure using a rotary evaporator and an 80° C. water bath. The resulting solid was then dried in a vacuum oven overnight at 110° C. The solid was then calcined in air at 400° C. for three hours.

0.46 Grams of the calcined solid was wetted with 0.5 mL of water, and then impregnated with 0.0396 g of tetraamineplatinum (II) nitrate in 0.5 mL of water. The mixture was stirred for 15 minutes, then dried overnight under vacuum at 110° C. After cooling to room temperature, the material was transferred to a ceramic boat and calcined in air at 400° C. for three hours.

Other PtW/TiO$_2$ catalysts containing 1, 2, or 4 wt % Pt in combination with 4, 10, 15, or 20 wt % W were prepared according to Catalyst Preparation Method B using the appropriate amounts of ammonium tungsten oxide hydrate, TiO$_2$, and tetraamineplatinum (II) nitrate. Catalysts prepared by Method B were used in Examples 78-89. Results are given in Table 9.

Examples 71-82

Hydrodeoxygenation of 126HT to 16HD Using PtW/TiO$_2$ Catalysts Containing (x % Pt, y % W)

Examples 71-82 were performed following the procedure of Examples 1-11 except using the PtW/TiO$_2$ catalysts containing (x % Pt, y % W) and temperatures as indicated in Table 9. Results are presented in Table 9.

TABLE 9

Conversion of 126HT to 16HD Using PtW/TiO$_2$ (x % Pt y % W) at 200° C. and 1000 psig $H_2$.

| | Catalyst * | % | % Yield | | | | | |
|---|---|---|---|---|---|---|---|---|
| Ex | wt % M1, wt % M2 | Conv | 16HD | THPM | 12HD | 15HD | 1H | 1P |
| 71 | PtW/TiO$_2$ 1% Pt, 4% W | 93.7 | 58.3 | 0.9 | 1.5 | 3.7 | 15.0 | 0.6 |
| 72 | PtW/TiO$_2$ 2% Pt, 4% W | 91.2 | 58.5 | 1.0 | 1.7 | 4.1 | 10.4 | 0.4 |
| 73 | PtW/TiO$_2$ 4% Pt, 4% W | 95.9 | 50.7 | 0.2 | 0.0 | 2.3 | 20.6 | 1.0 |
| 74 | PtW/TiO$_2$ 1% Pt, 10% W | 45.4 | 22.3 | 4.9 | 1.7 | 1.5 | 4.1 | 0.0 |
| 75 | PtW/TiO$_2$ 2% Pt, 10% W | 71.0 | 38.4 | 3.6 | 3.1 | 2.8 | 7.3 | 0.0 |
| 76 | PtW/TiO$_2$ 4% Pt, 10% W | 97.2 | 49.7 | 1.1 | 1.2 | 3.2 | 21.9 | 0.5 |
| 77 | PtW/TiO$_2$ 1% Pt, 15% W | 45.6 | 23.5 | 4.9 | 1.7 | 1.7 | 4.1 | 0.0 |
| 78 | PtW/TiO$_2$ 2% Pt, 15% W | 72.1 | 39.0 | 4.0 | 1.7 | 2.7 | 8.2 | 0.0 |
| 79 | PtW/TiO$_2$ 4% Pt, 15% W | 99.3 | 41.9 | 0.7 | 0.0 | 1.8 | 27.7 | 0.7 |
| 80 | PtW/TiO$_2$ 1% Pt, 20% W | 53.3 | 27.9 | 5.5 | 2.3 | 1.9 | 5.1 | 0.0 |
| 81 | PtW/TiO$_2$ 2% Pt, 20% W | 74.2 | 40.6 | 3.6 | 1.6 | 3.3 | 9.0 | 0.2 |
| 82 | PtW/TiO$_2$ 4% Pt, 20% W | 99.4 | 40.5 | 0.5 | 0.0 | 2.7 | 27.1 | 0.8 |

* For catalysts containing TiO$_2$, the TiO$_2$ supports were Aerolyst-7708 except where indicated otherwise.

Examples 83-190

Hydrodeoxygenation of 1,2,6-Hexanetriol to 1,6-Hexanediol Using M1M2/Support Catalysts in Batch Mode (with Pre-Reduction of the Catalyst)

In each of Examples 83-205, the conversion of 1,2,6-hexanetriol (126HT) to a reaction mixture comprising 1,6-hexanediol (16HD) was performed according to the following procedure. Approximately 1 g of an aqueous solution of 126HT (5 weight percent) and approximately 50 mg of the M1M2/support catalyst indicated in Table 10 were placed into a 1.5 mL pressure vessel containing a stir bar. The vessel was charged with $H_2$ to a pre-reduction pressure of about 145-150 psi, and then the pressure vessel was heated to the reaction temperature shown in Table 10. The contents were stirred for 1 hour before the pressure was raised to 1000 psig $H_2$. The reaction pressure and temperature were maintained for 4 hours. The vessel was then cooled to room temperature. The reaction mixture was filtered and the reaction solution analyzed using GC methods calibrated with internal standards.

Catalysts used in Examples 83-150, temperatures, percent conversion of 126HT substrate, and percent selectivity to 16HD are presented in Table 10.

Catalysts used in Examples 151-190, temperatures, percent conversion of 126HT substrate, percent selectivity to 16HD, and percent selectivity to THPM are presented in Table 11.

TABLE 10

Conversion of 126HT to 16HD Using M1M2/Support Catalysts

| Ex | Temp ° C. | Support * | M1 | M2 | M1 wt % | M2/M1 molar ratio | % Conv | % Sel to 16HD |
|---|---|---|---|---|---|---|---|---|
| 83 | 180 | TiO2 | Ir | Mo | 4 | 1 | 42.52 | 22.4 |
| 84 | 160 | Al2O3 | Ir | Re | 4 | 0.5 | 10.11 | 23.6 |
| 85 | 180 | CBV780 | Ir | Re | 4 | 1 | 96.66 | 39.2 |
| 86 | 160 | Celite | Ir | Re | 4 | 0.5 | 43.51 | 23.4 |
| 87 | 160 | H—Y 120/20 | Ir | Re | 4 | 0.5 | 80.76 | 52.4 |
| 88 | 160 | MgO | Ir | Re | 4 | 1 | 14.89 | 5.7 |
| 89 | 160 | SiO2 | Ir | Re | 4 | 0.5 | 49.78 | 18.9 |
| 90 | 180 | TiO2 | Ir | Re | 4 | 1 | 81.41 | 39.7 |
| 91 | 160 | Zeocat ZSM-5 PZ-2/50H | Ir | Re | 4 | 0.5 | 86.22 | 49.9 |
| 92 | 160 | Zeolyst CP814E H-Beta | Ir | Re | 4 | 0.5 | 64.12 | 20.7 |
| 93 | 180 | CBV780 | Ir | W | 4 | 1 | 62.10 | 26.0 |
| 94 | 160 | MgO | Ir | W | 4 | 1 | 11.03 | 1.2 |
| 95 | 180 | TiO2 | Ir | W | 4 | 1 | 54.99 | 41.3 |
| 96 | 180 | TiO2 | Pd | Mo | 4 | 1 | 4.43 | 14.4 |
| 97 | 160 | MgO | Pd | Re | 4 | 1 | 1.46 | 5.5 |
| 98 | 180 | TiO2 | Pd | Re | 4 | 1 | 23.95 | 24.3 |
| 99 | 160 | MgO | Pd | W | 4 | 1 | 11.52 | 1.2 |
| 100 | 180 | TiO2 | Pd | W | 4 | 1 | 13.11 | 26.2 |
| 101 | 180 | Silica-Alumina | Pt | Co | 4 | 0.5 | 7.17 | 7.2 |
| 102 | 180 | CBV780 | Pt | Co | 4 | 0.5 | 29.70 | 19.6 |
| 103 | 180 | Al2O3 | Pt | Mn | 4 | 0.5 | 3.78 | 2.8 |
| 104 | 180 | Celite | Pt | Mn | 4 | 0.5 | 4.02 | 2.0 |
| 105 | 180 | Silica-Alumina | Pt | Mn | 4 | 0.5 | 10.78 | 11.3 |
| 106 | 180 | SiO2 | Pt | Mn | 4 | 0.5 | 4.50 | 1.6 |
| 107 | 180 | CBV780 | Pt | Mn | 4 | 0.5 | 82.91 | 14.9 |
| 108 | 180 | Al2O3 | Pt | Mo | 4 | 0.5 | 4.13 | 13.8 |
| 109 | 180 | Celite | Pt | Mo | 4 | 0.5 | 4.78 | 1.6 |
| 110 | 180 | Silica-Alumina | Pt | Mo | 4 | 0.5 | 17.25 | 27.5 |
| 111 | 180 | SiO2 | Pt | Mo | 4 | 0.5 | 8.84 | 17.3 |
| 112 | 180 | TiO2 | Pt | Mo | 4 | 0.5 | 47.45 | 20.4 |
| 113 | 180 | TiO2 | Pt | Mo | 4 | 1 | 38.28 | 24.8 |
| 114 | 180 | CBV780 | Pt | Mo | 4 | 0.5 | 75.65 | 31.5 |
| 115 | 180 | Al2O3 | Pt | Re | 4 | 0.5 | 76.72 | 39.0 |
| 116 | 180 | CBV780 | Pt | Re | 4 | 1 | 90.70 | 32.2 |
| 117 | 180 | Celite | Pt | Re | 4 | 0.5 | 3.47 | 2.4 |
| 118 | 180 | H—Y 120/20 | Pt | Re | 4 | 0.5 | 99.75 | 23.9 |
| 119 | 180 | LSX | Pt | Re | 4 | 0.5 | 5.82 | 1.9 |
| 120 | 180 | NH4 Mordenite CBV-20A | Pt | Re | 4 | 0.5 | 49.07 | 32.8 |
| 121 | 180 | SiO2 | Pt | Re | 4 | 0.5 | 11.18 | 14.6 |
| 122 | 180 | TiO2 | Pt | Re | 4 | 0.5 | 62.58 | 42.7 |
| 123 | 180 | TiO2 | Pt | Re | 0.5 | 1 | 7.73 | 33.3 |
| 124 | 180 | TiO2 | Pt | Re | 4 | 1 | 20.46 | 39.0 |
| 125 | 180 | Zeocat ZSM-5 PZ-2/50H | Pt | Re | 4 | 0.5 | 92.74 | 37.2 |
| 126 | 180 | Zeolyst CBV780 | Pt | Re | 4 | 0.5 | 95.71 | 34.8 |
| 127 | 180 | Zeolyst CP814E H-Beta | Pt | Re | 4 | 0.5 | 98.30 | 38.1 |
| 128 | 180 | Al2O3 | Pt | V | 4 | 0.5 | 5.84 | 8.3 |
| 129 | 180 | Celite | Pt | V | 4 | 0.5 | 8.54 | 1.1 |
| 130 | 180 | Silica-Alumina | Pt | V | 4 | 0.5 | 9.89 | 12.3 |
| 131 | 180 | SiO2 | Pt | V | 4 | 0.5 | 5.31 | 10.4 |
| 132 | 180 | CBV780 | Pt | V | 4 | 0.5 | 73.13 | 13.6 |
| 133 | 180 | Al2O3 | Pt | W | 4 | 0.5 | 7.90 | 19.4 |
| 134 | 180 | Celite | Pt | W | 4 | 0.5 | 5.19 | 26.4 |
| 135 | 180 | H—Y 120/20 | Pt | W | 4 | 0.5 | 75.74 | 22.9 |
| 136 | 180 | MgO | Pt | W | 4 | 1 | 4.51 | 2.7 |
| 137 | 180 | Silica-Alumina | Pt | W | 4 | 0.5 | 22.73 | 58.0 |
| 138 | 180 | SiO2 | Pt | W | 4 | 0.5 | 23.48 | 56.8 |
| 139 | 180 | SiO2 | Pt | W | 10 | 1 | 97.06 | 70.8 |
| 140 | 180 | TiO2 | Pt | W | 4 | 0.5 | 60.52 | 62.1 |
| 141 | 180 | TiO2 | Pt | W | 4 | 1 | 85.79 | 84.1 |
| 142 | 180 | TiO2 | Pt | W | 2 | 1 | 44.48 | 75.0 |
| 143 | 180 | TiO2-CBV780 | Pt | W | 4 | 1 | 80.82 | 66.4 |
| 144 | 180 | CBV780 | Pt | W | 4 | 0.5 | 64.34 | 35.5 |
| 145 | 180 | CBV780 | Pt | W | 4 | 1 | 87.16 | 42.8 |
| 146 | 180 | Al2O3 | Pt | Zr | 4 | 0.5 | 4.99 | 5.5 |
| 147 | 180 | Celite | Pt | Zr | 4 | 0.5 | 4.66 | 2.9 |
| 148 | 180 | Silica-Alumina | Pt | Zr | 4 | 0.5 | 10.12 | 11.4 |
| 149 | 180 | SiO2 | Pt | Zr | 4 | 0.5 | 2.74 | 5.7 |
| 150 | 180 | CBV780 | Pt | Zr | 4 | 0.5 | 61.24 | 17.4 |

* For catalysts containing $TiO_2$, the $TiO_2$ supports were Aerolyst-7708 except where indicated otherwise.

TABLE 11

Conversion of 126HT to 16HD Using M1M2/Support Catalysts

| Ex | Temp (° C.) | Support * | M1 | M2 | M1 wt % | M2/M1 molar ratio | % Conv | % Sel to 1,6 HD | % Sel to THPM |
|---|---|---|---|---|---|---|---|---|---|
| 151 | 180 | TiO2 | Ir | Mo | 4 | 1 | 42.52 | 7.06 | 22.4 |
| 152 | 160 | Al2O3 | Ir | Re | 4 | 0.5 | 10.11 | 18.79 | 23.6 |
| 153 | 180 | CBV780 | Ir | Re | 4 | 1 | 96.66 | 10.65 | 39.2 |
| 154 | 160 | Celite | Ir | Re | 4 | 0.5 | 43.51 | 4.63 | 23.4 |
| 155 | 160 | H—Y 120/20 | Ir | Re | 4 | 0.5 | 80.76 | 13.90 | 52.4 |

TABLE 11-continued

Conversion of 126HT to 16HD Using M1M2/Support Catalysts

| Ex | Temp (° C.) | Support * | M1 | M2 | M1 wt % | M2/M1 molar ratio | % Conv | % Sel to 1,6 HD | % Sel to THPM |
|---|---|---|---|---|---|---|---|---|---|
| 156 | 160 | MgO | Ir | Re | 4 | 1 | 14.89 | 4.61 | 5.7 |
| 157 | 160 | SiO2 | Ir | Re | 4 | 0.5 | 49.78 | 3.77 | 18.9 |
| 158 | 180 | TiO2 | Ir | Re | 4 | 1 | 81.41 | 3.06 | 39.7 |
| 159 | 160 | Zeocat ZSM-5 PZ-2/50H | Ir | Re | 4 | 0.5 | 86.22 | 21.33 | 49.9 |
| 160 | 160 | Zeolyst CP814E H-Beta | Ir | Re | 4 | 0.5 | 64.12 | 68.16 | 20.7 |
| 161 | 180 | CBV780 | Ir | W | 4 | 1 | 62.10 | 59.65 | 26.0 |
| 162 | 160 | MgO | Ir | W | 4 | 1 | 11.03 | 6.10 | 1.2 |
| 163 | 180 | Al2O3 | Pt | Mn | 4 | 0.5 | 3.78 | 2.8 | 15.90 |
| 164 | 180 | Celite | Pt | Mn | 4 | 0.5 | 4.02 | 2.0 | 26.30 |
| 165 | 180 | Silica-Alumina | Pt | Mn | 4 | 0.5 | 10.78 | 11.3 | 31.52 |
| 166 | 180 | SiO2 | Pt | Mn | 4 | 0.5 | 4.50 | 1.6 | 24.68 |
| 167 | 180 | CBV780 | Pt | Mn | 4 | 0.5 | 82.91 | 14.9 | 43.35 |
| 168 | 180 | Al2O3 | Pt | Mo | 4 | 0.5 | 4.13 | 13.8 | 18.00 |
| 169 | 180 | Celite | Pt | Mo | 4 | 0.5 | 4.78 | 1.6 | 22.10 |
| 170 | 180 | Silica-Alumina | Pt | Mo | 4 | 0.5 | 17.25 | 27.5 | 17.58 |
| 171 | 180 | SiO2 | Pt | Mo | 4 | 0.5 | 8.84 | 17.3 | 10.70 |
| 172 | 180 | TiO2 | Pt | Mo | 4 | 0.5 | 52.16 | 20.2 | 4.91 |
| 173 | 180 | CBV780 | Pt | Mo | 4 | 0.5 | 75.65 | 31.5 | 46.08 |
| 174 | 180 | Al2O3 | Pt | Re | 4 | 0.5 | 76.72 | 39.0 | 1.92 |
| 175 | 180 | CBV780 | Pt | Re | 4 | 1 | 90.70 | 32.2 | 25.51 |
| 176 | 180 | Celite | Pt | Re | 4 | 0.5 | 3.47 | 2.4 | 25.73 |
| 177 | 180 | H—Y 120/20 | Pt | Re | 4 | 0.5 | 99.75 | 23.9 | 67.86 |
| 178 | 180 | LSX | Pt | Re | 4 | 0.5 | 5.14 | 2.1 | 22.49 |
| 179 | 180 | NH4 Mordenite CBV-20A | Pt | Re | 4 | 0.5 | 49.07 | 32.8 | 46.65 |
| 180 | 180 | SiO2 | Pt | Re | 4 | 0.5 | 11.18 | 14.6 | 11.46 |
| 181 | 180 | TiO2 | Pt | Re | 4 | 0.5 | 60.85 | 32.6 | 4.72 |
| 182 | 180 | TiO2 | Pt | Re | 4 | 0.5 | 52.76 | 35.4 | 7.88 |
| 183 | 180 | Zeocat ZSM-5 PZ-2/50H | Pt | Re | 4 | 0.5 | 92.74 | 37.2 | 42.48 |
| 184 | 180 | CBV780 | Pt | Re | 4 | 0.5 | 95.71 | 34.8 | 32.51 |
| 185 | 180 | Zeolyst CP814E H-Beta | Pt | Re | 4 | 0.5 | 98.30 | 38.1% | 37.35 |
| 186 | 180 | Al2O3 | Pt | V | 4 | 0.5 | 5.84 | 8.3 | 14.31 |
| 187 | 180 | Celite | Pt | V | 4 | 0.5 | 8.54 | 1.1 | 26.54 |
| 188 | 180 | Silica-Alumina | Pt | V | 4 | 0.5 | 9.89 | 12.3 | 38.06 |
| 189 | 180 | SiO2 | Pt | V | 4 | 0.5 | 5.31 | 10. | 11.13 |
| 190 | 180 | CBV780 | Pt | V | 4 | 0.5 | 73.13 | 13.6 | 51.56 |

* For catalysts containing TiO$_2$, the TiO$_2$ supports were Aerolyst-7708 except where indicated otherwise.

Examples 191-228

Hydrodeoxygenation of THPM to 16HD Using M1M2/Support Catalysts

Examples 191-228 were performed following the procedure of Examples 83-150 except using an aqueous solution of 5 wt % THPM as the substrate and the M1M2/support catalysts and temperatures indicated in Table 12. Percent conversion of THPM substrate and percent selectivity to 16HD results are presented in Table 12.

TABLE 12

Conversion of THPM to 16HD Using M1M2/Support Catalysts at 180° C. and 1000 psig H$_2$

| Ex | Catalyst * (M1M2/Support) | M1 | M2 | M1 wt % | M2/M1 Molar Ratio | % Conv | % Sel to 16HD |
|---|---|---|---|---|---|---|---|
| 191 | PtW/Al2O3 | Pt | W | 4 | 0.5 | 5.91 | 38.6 |
| 192 | PtW/Celite | Pt | W | 4 | 0.5 | 1.07 | 0.0 |
| 193 | PtW/CeO2 | Pt | W | 4 | 0.5 | 0.22 | 39.8 |
| 194 | PtW/H—Y(120/20) | Pt | W | 4 | 0.5 | 8.66 | 75.0 |
| 195 | PtW/Sibunit # 1 Carbon | Pt | W | 4 | 0.5 | 1.58 | 8.8 |
| 196 | PtW/Sibunit # 2 Carbon | Pt | W | 4 | 0.5 | 1.64 | 26.0 |
| 197 | PtW/Silica-Alumina | Pt | W | 4 | 0.5 | 11.71 | 78.0 |
| 198 | PtW/SiO2 | Pt | W | 4 | 0.5 | 23.36 | 74.2 |
| 199 | PtW/TiO2 | Pt | W | 4 | 0.5 | 72.67 | 84.7 |
| 200 | PtW/TiO2 | Pt | W | 0.5 | 1 | 1.08 | 4.8 |
| 201 | PtW/TiO2 | Pt | W | 4 | 1 | 56.95 | 88.8 |
| 202 | PtW/Zeolyst CBV780 | Pt | W | 4 | 1 | 35.15 | 85.9 |
| 203 | PtW/Zeolyst CBV780 | Pt | W | 4 | 0.5 | 16.60 | 67.8 |
| 204 | PtMo/Zeolyst CBV780 | Pt | Mo | 4 | 0.5 | 17.09 | 69.2 |
| 205 | PtRe/Al2O3 | Pt | Re | 4 | 0.5 | 47.55 | 67.7 |
| 206 | PtRe/CBV780 | Pt | Re | 4 | 1 | 33.79 | 60.7 |
| 207 | PtRe/Celite | Pt | Re | 4 | 0.5 | 2.82 | 1.0 |
| 208 | PtRe/CeO2 | Pt | Re | 4 | 0.5 | 0.05 | 16.2 |
| 209 | PtRe/H—Y 120/20 | Pt | Re | 4 | 0.5 | 32.68 | 70.5 |
| 210 | PtRe/LSX | Pt | Re | 4 | 0.5 | 2.52 | 1.5 |
| 211 | PtRe/NH4(Mordenite CBV-20A) | Pt | Re | 4 | 0.5 | 21.23 | 61.7 |
| 212 | PtRe/SiO2 | Pt | Re | 4 | 0.5 | 1.75 | 33.7 |
| 213 | PtRe/TiO2 | Pt | Re | 4 | 0.5 | 41.29 | 73.4 |

TABLE 12-continued

Conversion of THPM to 16HD Using M1M2/Support Catalysts at 180° C. and 1000 psig $H_2$

| Ex | Catalyst * (M1M2/Support) | M1 | M2 | M1 wt % | M2/M1 Molar Ratio | % Conv | % Sel to 16HD |
|---|---|---|---|---|---|---|---|
| 214 | PtRe/TiO2-Aerolyst 7708 | Pt | Re | 4 | 1 | 45.28 | 79.1 |
| 215 | PtRe/TiO2-Aerolyst 7708 | Pt | Re | 0.5 | 0.5 | 5.22 | 73.4 |
| 216 | PtRe/TiO2-Aerolyst 7708 | Pt | Re | 0.5 | 1 | 5.73 | 74.0 |
| 217 | PtRe/Zeocat(ZSM-5) (PZ-2/50H) | Pt | Re | 4 | 0.5 | 41.20 | 67.7 |
| 218 | PtRe/Zeolyst CBV780 | Pt | Re | 4 | 0.5 | 41.36 | 75.7 |
| 219 | PtRe/Zeolyst CBV780 | Pt | Re | 4 | 0.75 | 48.00 | 74.3 |
| 220 | PtRe/Zeolyst CBV780 | Pt | Re | 4 | 1 | 38.39 | 72.5 |
| 221 | PtRe/Zeolyst CBV780 | Pt | Re | 0.5 | 1 | 4.11 | 56.8 |
| 222 | PtRe/Zeolyst(CP814E) H-Beta MR350 | Pt | Re | 4 | 0.5 | 44.10 | 73.2 |
| 223 | PtV/Al2O3 | Pt | V | 4 | 0.5 | 4.72 | 3.8 |
| 224 | PtV/Celite | Pt | V | 4 | 0.5 | 0.51 | 2.8 |
| 225 | PtV/Celite | Pt | V | 4 | 0.5 | 2.43 | 1.0 |
| 226 | PtV/Silica-Alumina | Pt | V | 4 | 0.5 | 1.65 | 29.4 |
| 227 | PtV/SiO2 | Pt | V | 4 | 0.5 | 2.0 | 12.4 |
| 228 | PtV/Zeolyst CBV780 | Pt | V | 4 | 0.5 | 5.07 | 42.6 |

* In table 12, for catalysts containing $TiO_2$, the $TiO_2$ supports were Aerolyst-7711 except where indicated otherwise.

Examples 229-255

Hydrodeoxygenation of Tetrahydrofuran-2,5-Dimethanol to 16HD Using M1M2/Support Catalysts Examples 229-255 were performed following the procedure of Examples 83-150 except using an aqueous solution of 5 wt % tetrahydrofuran-2,5-dimethanol as the substrate, the temperatures, and the M1M2/support catalysts indicated in Table 13. These catalysts contained 4 wt % M1 and had an M1/M2 molar ratio of 1. Table 13 also includes percent conversion of tetrahydrofuran-2,5-dimethanol substrate and percent selectivity to 16HD results.

TABLE 13

Conversion of Tetrahydrofuran-2,5-dimethanol to 16HD using M1M2/Support Catalysts (1000 psig H2; M1 wt % = 4; M1/M2 = 1)

| Ex | Temp (° C.) | Catalyst * (M1M2/Support) | M 1 | M2 | % Conv | % Sel to 126HT | % Sel to 16HD |
|---|---|---|---|---|---|---|---|
| 229 | 160 | IrRe/Al2O3 | Ir | Re | 5.38 | 25.47 | 1.0 |
| 230 | 160 | IrRe/Celite | Ir | Re | 36.47 | 53.86 | 1.7 |
| 231 | 160 | IrRe/H—Y 120/20 | Ir | Re | 100.00 | 11.45 | 45.5 |
| 232 | 160 | IrRe/SiO2 | Ir | Re | 12.09 | 70.28 | 1.3 |
| 233 | 160 | IrRe/Zeocat ZSM-5 PZ-2/50H | Ir | Re | 19.74 | 40.29 | 4.7 |
| 234 | 160 | IrRe/Zeolyst CP814E H-Beta | Ir | Re | 10.80 | 45.28 | 2.9 |
| 235 | 180 | PtMn/Silica-Alumina | Pt | Mn | 2.26 | 57.19 | 1.6 |
| 236 | 180 | PtMn/CBV780 | Pt | Mn | 6.52 | 36.39 | 3.3 |
| 237 | 180 | PtMo/Silica-Alumina | Pt | Mo | 11.53 | 57.11 | 4.5 |
| 238 | 180 | PtMo/TiO2 | Pt | Mo | 40.43 | 54.12 | 10.8 |
| 239 | 180 | PtMo/TiO2-7711 | Pt | Mo | 41.16 | 53.06 | 10.8 |
| 240 | 180 | PtMo/CBV780 | Pt | Mo | 47.30 | 30.12 | 20.3 |
| 241 | 180 | PtRe/Al2O3 | Pt | Re | 69.31 | 42.97 | 21.1 |
| 242 | 180 | PtRe/H—Y 120/20 | Pt | Re | 38.42 | 41.45 | 15.5 |
| 243 | 180 | PtRe/NH4 Mordenite CBV-20A | Pt | Re | 22.75 | 44.65 | 7.9 |
| 244 | 180 | PtRe/TiO2 | Pt | Re | 67.62 | 41.89 | 17.9 |
| 245 | 180 | PtRe/TiO2-7711 | Pt | Re | 56.15 | 52.67 | 18.8 |
| 246 | 180 | PtRe/Zeocat ZSM-5 PZ-2/50H | Pt | Re | 52.65 | 7.66 | 15.3 |
| 247 | 180 | PtRe/CBV780 | Pt | Re | 63.35 | 22.43 | 15.9 |
| 248 | 180 | PtRe/Zeolyst CP814E H-Beta | Pt | Re | 27.12 | 30.10 | 8.8 |
| 249 | 180 | PtV/Silica-Alumina | Pt | V | 3.29 | 34.85 | 1.4 |
| 250 | 180 | PtW/H—Y 120/20 | Pt | W | 19.24 | 41.29 | 17.9 |
| 251 | 180 | PtW/Silica-Alumina | Pt | W | 30.01 | 72.86 | 10.8 |
| 252 | 180 | PtW/SiO2 | Pt | W | 21.93 | 80.30 | 5.2 |
| 253 | 180 | PtW/TiO2 | Pt | W | 53.08 | 62.81 | 23.3 |
| 254 | 180 | PtW/TiO2-7711 | Pt | W | 23.44 | 81.62 | 9.6 |
| 255 | 180 | PtW/CBV780 | Pt | W | 31.37 | 55.73 | 19.0 |

* For catalysts containing $TiO_2$, the $TiO_2$ supports were Aerolyst-7708 except where indicated otherwise.

Example 256

Conversion of 1,2,6-Hexanetriol to a Reaction Mixture Comprising 1,6-Hexanediol in a Continuous Trickle Bed Reactor A M1M2/support catalyst containing Pt/W (1:1) supported on $TiO_2$ was prepared according to the following procedure. 32.2 Grams of catalyst support (Aerolyst 7708 $TiO_2$) as received from the vendor was first crushed and sieved to a particle size range of 1 to 1.2 mm. The support was then added to a flask and wetted with approximately 32 mL of deionized water. The wetted support was then mixed with an additional 35 mL deionized water containing 2.77 g of dissolved tetraamineplatinum (II) nitrate M1-salt to form a slurry. The support/M1-salt slurry was then stirred for 15 minutes. The flask was then placed onto a rotary evaporator and water was removed at 80° C. under reduced pressure until the catalyst reached incipient wetness. The catalyst was then further dried overnight (17 h) in a vacuum oven held at 110° C. The dried catalyst was allowed to cool to room temperature, then was wetted again with of 35 mL of deionized water. The wetted support was then mixed with an additional 105 mL of deionized water containing 1.87 g of dissolved ammonium tungsten oxide hydrate M2-salt to form a slurry. The slurry was then stirred for 15 minutes. The flask was then placed onto a rotary evaporator and water was removed at 80° C. under reduced pressure until the catalyst reached incipient wetness. The catalyst was then further dried overnight (17 h) in a vacuum oven held at 110° C. After cooling to room temperature, the material was transferred to a ceramic boat and calcined in air at 400° C. for three hours. The catalyst was used to hydrodeoxygenate 126HT to a reaction mixture comprising 16HD according to the following procedure.

The conversion of 126HT to a reaction mixture comprising 16HD was conducted in a vertical 21 mm internal diameter 316 stainless steel fixed bed reactor. The reactor was initially loaded with 21.14 g of the Pt/W (1:1) on Aerolyst 7708 TiO$_2$ catalyst, which was held in place by about 20 g of 1 mm inert corundum spheres on both sides of the catalyst bed.

The reactor was pressurized with nitrogen to 1000 psi using a flow rate of 192 sccm. The run was started by introducing a 4.0 wt % 126HT in water feed to the inlet at the top of the reactor at a flow rate of 0.192 mL min-1. At the same time the reactor heating was started. Once the reactor reached 140° C. the nitrogen feed was turned off and the hydrogen feed was simultaneously started with a flow rate of 192 sccm.

During the run liquid product was collected in a 1 L chilled product receiver. After 2 days on stream the reactor temperature was increased to 160° C. After 5 days on stream a one hour averaged steady state sample was collected by first draining the product receiver and then allowing it to refill over a one hour time period. The sample was then drained from the product receiver, weighed and analyzed by gas chromatography. All major compounds were identified and quantified using analytical standards. The 11.55 g sample solution contained 0.141 g of 126HT (69.7% conversion based on 126HT fed) and 0.205 g of 16HD (50.0% molar yield based on 126HT fed).

Example 257

Conversion of 1,2,6-Hexanetriol, 2-Hydroxymethyltetrahydropyran, and Tetrahydrofuran-2,5-Dimethanol Feedstocks (Separately) to a Reaction Mixture Comprising 1,6-Hexanediol in a Continuous Trickle Bed Reactor A M1M2/support catalyst containing Ni/W (1:1) supported on TiO$_2$ was prepared according to the following procedure. 28.8 Grams of catalyst support (Aerolyst 7708 TiO$_2$) as received from the vendor was first crushed and sieved to a particle size range of 1 to 1.2 mm. The support was then added to a flask and wetted with approximately 30 mL of deionized water. The wetted support was then mixed with an additional 10 mL deionized water containing 5.95 g of dissolved nickel (II) nitrate hexahydrate M1-salt to form a slurry. The support/M1-salt slurry was then stirred for 15 minutes. The flask was then placed onto a rotary evaporator and water was removed at 80° C. under reduced pressure until the catalyst reached incipient wetness. The catalyst was then further dried overnight (17 h) in a vacuum oven held at 110° C. The dried catalyst was allowed to cool to room temperature, then was wetted again with of 30 mL of deionized water. The wetted support was then mixed with an additional 300 mL of deionized water containing 5.34 g of dissolved ammonium tungsten oxide hydrate M2-salt to form a slurry. The slurry was then stirred for 15 minutes. The flask was then placed onto a rotary evaporator and water was removed at 80° C. under reduced pressure until the catalyst reached incipient wetness. The catalyst was then further dried overnight (17 h) in a vacuum oven held at 110° C. After cooling to room temperature, the material was transferred to a ceramic boat and calcined in air at 400° C. for three hours. The catalyst was used to hydrodeoxygenate several oxygenated feedstocks in sequence to a reaction mixture comprising 16HD according to the following procedure.

A vertical 21 mm internal diameter 316 stainless steel fixed bed reactor was initially loaded with 20.04 g of the Ni/W (1:1) on Aerolyst 7708 TiO$_2$ catalyst held in place by about 20 g of 1 mm inert corundum spheres on both sides of the catalyst bed.

The reactor was pressurized with nitrogen to 1000 psi using a flow rate of 158 sccm. The run was started by introducing a 4.7 wt % 126HT in water feed to the inlet at the top of the reactor at a flow rate of 0.158 ml min-1. At the same time the reactor heating was started. Once the reactor reached 235° C. the nitrogen feed was turned off and the hydrogen feed was simultaneously started with a flow rate of 158 sccm.

During the run liquid product was collected in a 1 L chilled product receiver. After 9 days on stream the reactor temperature was increased to 250° C. and the reactor pressure was increased to 1500 psi. After 10 days on stream a one hour averaged steady state sample was collected by first draining the product receiver and then allowing it to refill over a one hour time period. The sample was then drained from the product receiver, weighed and analyzed by gas chromatography. All major compounds were identified and quantified using analytical standards. The 18.54 g sample solution contained 0.069 g of 126HT (92.1% conversion based on 126HT fed) and 0.229 g of 16HD (29.5% molar yield based on 126HT fed).

After 57 days on stream the liquid feed was switched to a 4.7 wt % 2-hydroxymethyltetrahydropyran in water solution with a flow rate of 0.158 mL min$^{-1}$. After 58 days on stream a one hour averaged steady state sample was collected. The 14.67 g sample solution contained 0.595 g of 2-hydroxymethyltetrahydropyran (14.7% conversion based on 2-hydroxymethyltetrahydropyran fed) and 0.439 g of 16HD (6.2% molar yield based on 2-hydroxymethyltetrahydropyran fed).

After 65 days on stream the liquid feed was switched to a 4.7 wt % tetrahydrofuran-2,5-dimethanol in water solution with a flow rate of 0.158 mL min$^{-1}$ at the same time the reactor temperature was lowered to 240° C. After 66 days on stream a one hour averaged steady state sample was collected. The 12.95 g sample solution contained 0.392 g of tetrahydrofuran-2,5-dimethanol (37.3% conversion based on tetrahydrofuran-2,5-dimethanol fed) and 0.019 g of 16HD (3.5% molar yield based on tetrahydrofuran-2,5-dimethanol fed).

Example 258

Conversion of 1,2,6-Hexanetriol to a Reaction Mixture Comprising 1,6-Hexanediol in a Continuous Trickle Bed Reactor This Example was carried out in a stainless steel (SS316) continuous trickle bed reactor (ID=0.4 cm) using the following procedure.

The reactor was packed with approximately 1 mL of catalyst. If the catalyst was not pre-reduced, the following procedure was used for in situ reduction: the reactor was heated at a rate of 1° C./min under forming gas (5% H$_2$ in N$_2$) to the desired reduction temperature (see examples), where it was held for the desired hold-up time, typically 2-3 hours. The pre-reduced or in-situ reduced catalyst was used for running multiple reactions under varying reaction conditions (temperature, pressure, feed concentrations). The reactor temperature was adjusted to the target first reaction condition temperature and held overnight under forming gas and either water or aqueous substrate solution. Subsequently the first reaction condition started by changing the gas feed to 100% H$_2$ and the liquid feed to the desired aqueous substrate concentration. The liquid volumetric feed rate was adjusted to correspond to a target liquid hourly space velocity (LHSV), which was measured in units of mL liquid feed/mL catalyst/h. Unless otherwise specified, the ratio of the gas volumetric flowrate to the liquid volumetric flowrate as measured at ambient conditions (gas to oil ratio, GTO) was adjusted to a value of 4,000. Liquid effluent samples at each reaction condition were taken after continuous operation for a minimum of 24 hours. The liquid samples were analyzed by quantitative GC analysis.

For Example 258, the continuous reactor was charged with a PtW/TiO$_2$ catalyst having M1=Pt and M2=W such that the loading of Pt on TiO$_2$ was 4 wt % and the loading of W was such that the metal molar ratio of Pt/W=1.0. The catalyst was made according to Catalyst Preparation Method A. Aqueous solutions of 2.5 wt % 1,2,6-hexanetriol were used as the liquid feed. The liquid volumetric feed rate corresponded to a liquid hourly space velocity (LHSV) equal to 0.5 mL liquid feed/mL catalyst/h. Results at 200° C. are presented in Table 14.

About 100 mg of fresh catalyst was added to compensate for physical losses. A sample of the filtrate was analyzed by GC and GC/MS; results are given in Table 15.

For the second pass of this Example, the reactor was recharged with fresh feed solution and the second pass was conducted as described above for the first pass.

For the third pass of this Example, the reactor was recharged with fresh feed solution and the third pass was conducted as described above for the first pass.

For the fourth pass of this Example, the reactor was recharged with fresh feed solution and the fourth pass was started as described above for the first pass. GC analysis of a sample taken after a run time of 10 h revealed lower conversion when compared to the average of the previous passes. The reaction time was extended to 24 h at 160° C., followed by another 24 h at 180° C., before the reactor was allowed to cool to room temperature and the filtering and analysis procedure described for the first pass was followed.

Results for the filtered reaction product from each pass are presented in Table 15.

TABLE 14

Results for Example 258 (200° C.)

| GTO | Pressure (bar) | H$_2$ Content (%) | 1H | 1P | THPM | 12HD | 15HD | 16HD | 15PD | 1B | 12PD | 126HT | Conv. (%) | Mole Balance (%) |
|---|---|---|---|---|---|---|---|---|---|---|---|---|---|---|
| 100 | 69 | 20 | 4.40 | 2.41 | 3.80 | 12.71 | 2.09 | 18.76 | 3.93 | 0.00 | 1.20 | 30.89 | 69.10 | 83.30 |
| 100 | 69 | 50 | 3.27 | 1.00 | 2.37 | 8.64 | 2.76 | 20.07 | 3.20 | 0.00 | 0.00 | 50.20 | 49.80 | 93.36 |
| 100 | 69 | 100 | 2.65 | 0.58 | 1.71 | 6.28 | 3.90 | 31.19 | 2.50 | 0.00 | 0.00 | 41.13 | 58.87 | 92.95 |
| 1000 | 69 | 5 | 4.76 | 10.84 | 2.54 | 5.90 | 0.49 | 3.40 | 1.42 | 5.46 | 3.70 | 1.54 | 98.46 | 47.46 |
| 1000 | 69 | 20 | 4.27 | 4.76 | 3.60 | 12.51 | 3.21 | 13.95 | 7.35 | 1.04 | 2.35 | 20.51 | 79.49 | 77.35 |
| 1000 | 69 | 50 | 3.00 | 1.95 | 2.53 | 9.74 | 4.31 | 18.03 | 5.89 | 0.00 | 0.98 | 38.57 | 61.43 | 89.68 |
| 1000 | 69 | 100 | 2.37 | 1.00 | 1.95 | 8.45 | 5.04 | 20.95 | 4.69 | 0.00 | 0.49 | 41.90 | 58.10 | 89.69 |
| 100 | 100 | 50 | 0.00 | 0.00 | 1.38 | 3.00 | 0.95 | 9.06 | 1.05 | 0.00 | 0.00 | 86.88 | 13.12 | 105.44 |
| 100 | 100 | 100 | 0.52 | 0.00 | 1.49 | 3.00 | 1.96 | 18.94 | 1.08 | 0.00 | 0.00 | 72.82 | 27.18 | 103.92 |
| 1000 | 100 | 100 | 0.00 | 0.00 | 0.95 | 1.59 | 1.32 | 5.08 | 4.16 | 0.00 | 0.00 | 86.99 | 13.01 | 102.85 |
| 1000 | 100 | 50 | 0.00 | 0.00 | 1.62 | 2.18 | 1.18 | 3.23 | 5.80 | 0.00 | 0.00 | 84.92 | 15.08 | 102.15 |

Example 259

Conversion of 126HT to a Reaction Mixture Comprising 16HD Using a PtW/TiO$_2$ Catalyst Under Recycle Conditions A feed solution comprising 30 parts 126HT, 5 parts deionized water, and 65 parts n-hexanol was placed into a calibrated vessel.

For the first pass of Example 259, a 20.0 mL aliquot containing a net amount of 5.84 g of 126HT (6.00 g of 97% purity material) was transferred from the calibrated vessel into a stainless steel (SS316) pressure reactor equipped with a fritted sample line and a magnetic stir bar. Subsequently about 2.00 g of 4% PtW/TiO$_2$ catalyst (1:1 Pt:W on Aerolyst 7708 TiO$_2$) was added to the pressure reactor, which was then sealed, connected to a high pressure gas manifold, and purged with nitrogen gas (1000 psi) three times. About 800 psi of hydrogen was then added, the reactor heated to 160° C., and then the pressure was adjusted with hydrogen to about 1000 psi. The progress of the reaction was monitored by taking two 0.100 mL samples. After 10 h, the reactor was allowed to cool to room temperature within 2 hours and depressurized. The reaction product solution was diluted with n-propanol and a known amount of diethylene glycol diethyl ether as an internal standard and filtered through a standard 5 micron disposable filter. The remaining catalyst was washed with n-hexanol and returned to the reactor.

TABLE 15

Results for Reaction Product Solution Obtained for Each Pass of Example 259

| Pass | % Molar Yield 16HD | % Molar Yield THPM | % Molar Yield 12HD | % Molar Yield 15HD | % Molar Yield 15PD | Mass balance (molar %) | Conv (molar %) |
|---|---|---|---|---|---|---|---|
| 1 | 41 | 2 | <1 | 5 | 0 | 87 | 71 |
| 2 | 51 | 3 | <1 | 5 | 0 | 92 | 79 |
| 3 | 31 | 2 | <1 | 3 | 0 | 85 | 60 |
| 4 | 80 | 12 | <1 | 8 | 1 | 102 | 99 |

Example 260

Conversion of Tetrahydro-2,5-Furandimethanol to a Reaction Mixture Comprising 1,6-Hexanediol in a Continuous Trickle Bed Reactor This Example was carried out in a stainless steel (SS316) continuous trickle bed reactor (ID=0.4 cm) using the following procedure.

The reactor was packed with approximately 1 mL of catalyst prepared using catalyst synthesis method A. The catalyst was pre-reduced using the following procedure for in situ reduction: the reactor was heated at a rate of 1° C./min under forming gas (5% H$_2$ in N$_2$) to the 150°, where it was held for 3 hours. The in-situ reduced catalyst was used for running multiple reactions under varying reaction conditions (temperature, pressure, feed concentrations). The reactor temperature was adjusted to the target first reaction condition temperature and held overnight under forming gas and either water or aqueous substrate solution. Subsequently, the first reaction condition started by changing the gas feed to 100% $H_2$ and the liquid feed to the desired aqueous substrate concentration. The liquid volumetric feed rate was adjusted to correspond to a target liquid hourly space velocity (LHSV), which was measured in units of mL liquid feed/mL catalyst/h. Unless otherwise specified, the ratio of the gas volumetric flowrate to the liquid volumetric flowrate as measured at ambient conditions (gas to oil ratio, GTO) was adjusted to a value of 1,000. Liquid effluent samples at each reaction condition were taken after continuous operation for a minimum of 24 hours. The liquid samples were analyzed by quantitative GC analysis.

For Example 260, the continuous reactor was charged with a catalyst having M1=Pt and M2=W such that the loading of Pt on $ZrO_2$ (Saint-Gobain-NorPro SZ31107) was 4 wt % and the loading of W was such that the metal molar ratio of Pt/W=1.0; the catalyst was prepared according to Catalyst Preparation Method A. Aqueous solutions of 2.5 wt % THFdM were used as the liquid feed. The liquid volumetric feed rate corresponded to a liquid hourly space velocity (LHSV) equal to 0.5 mL liquid feed/mL catalyst/h. In one condition, the catalyst was operated at 100 bar and 140° C. At this condition, the observed conversion was 99 mol % with a molar yield to 16HD of 59%.

Example 261

Conversion of 1,2,6-HT to a Reaction Mixture Comprising 1,6-Hexanediol in a Continuous Trickle Bed Reactor Example 261 was carried out as described for Example 281 except that a solution of 2.5 wt % 126HT with 5 wt % $H_2O$ and the balance 1-hexanol was used as the liquid feed, and the temperature was 120° C. At this condition, the observed conversion was 100 mol % with a molar yield to 16HD of 71%.

Examples 262-269

Hydrodeoxygenation of THPM to 16HD Using a Physical Mixture of M1M2/Support Catalyst and an Additive These Examples were performed following the procedure of Examples 1-11 except adding 50 mg of an additive as noted in Table 16, and using a 140° C. temperature, an aqueous solution of 5 wt % 2-hydroxymethyltetrahydropyran (THPM) as the substrate, and a PtW/SiO$_2$ catalyst containing 4 wt % Pt and having Pt/W=1. The additive was not impregnated with a metal. Results are presented in Table 16.

TABLE 16

Conversion of THPM to 16HD Using M1M2/Support Catalysts in Combination with an Additive at 1000 psig $H_2$.

| Ex | Catalyst (M1M2/Support) | Additive | % Conversion | % Yield of 16HD |
|---|---|---|---|---|
| 262 | PtW/SiO$_2$ | None | 13.1 | 1.5 |
| 263 | PtW/SiO$_2$ | None | 12.8 | 1.6 |
| 264 | PtW/SiO$_2$ | SiO2 | 13.6 | 2.9 |
| 265 | PtW/SiO$_2$ | SiO2 | 16.2 | 4.8 |
| 266 | PtW/SiO$_2$ | SiO2 | 14.5 | 3.3 |
| 267 | PtW/SiO$_2$ | TiO2 | 55.5 | 47.0 |
| 268 | PtW/SiO$_2$ | TiO2 | 60.4 | 52.1 |
| 269 | PtW/SiO$_2$ | TiO2 | 60.2 | 50.6 |

The table above shows that, for a given M1M2/support catalyst, yield to 16HD at a given temperature was increased when an additive was present as a physical mixture with the catalyst. Compared to the Examples with PtW/SiO$_2$ alone and with extra non-impregnated SiO$_2$, PtW/SiO$_2$ is shown to have increased yield to 1,6-HD with the addition of TiO$_2$ at 140° C. (Examples 267-269). Other combinations are possible and are not limited to TiO$_2$.

Examples 270-273

Hydrodeoxygenation of THF-2-MeOH to 1,5-Pentanediol Using M1M2/Support Catalysts Examples 270-273 were performed following the procedure of Examples 1-11 except using the M1M2/support catalysts, a temperature of 140° C., and tetrahydrofurfuryl alcohol in place of 126HT. Results are shown in Table 17.

TABLE 17

Results for Examples 270-273

| Example | M1M2/Support Catalyst | % Yield of 15PD |
|---|---|---|
| 270 | PtW/TiO$_2$ 4% Pt; Pt/W = 1 | 56.1 |
| 271 | IrRe/CBV780 4% Ir; Ir/Re = 1 | 52.1 |
| 272 | IrRe/CBV780 4% Ir; Ir/Re = 1 | 45.0 |
| 273 | RhRe/CBV780 4% Rh, Rh/Re = 1 | 15.8 |

Comparative Examples A-R

Comparative Examples A-R were performed following the procedure of Examples 1-11 except using the catalysts and temperatures shown in Table 18. The M1M2/support catalysts were prepared according to Catalyst Preparation Method A. The M1/support catalysts were also prepared according to Catalyst Preparation Method A except that there was no addition of a second metal. The results show that no 16HD was observed in the reaction solutions.

TABLE 18

Results for Comparative Examples A-R.

| Comp Ex. | Temp (° C.) | Catalyst | % Conv | % Yield of 16HD |
|---|---|---|---|---|
| A | 140 | W/TiO$_2$ 4% W | 0 | 0 |
| B | 140 | W/TiO$_2$ 24% W | 0 | 0 |
| C | 250 | PdW/TiO$_2$ 4% Pd; Pd/W = 1 | 100 | 0 |
| D | 250 | IrRe/CBV780 4% Ir; Re/Ir = 1 | 100 | 0 |

TABLE 18-continued

Results for Comparative Examples A-R.

| Comp Ex. | Temp (° C.) | Catalyst | % Conv | % Yield of 16HD |
|---|---|---|---|---|
| E | 180 | RhMo/TiO$_2$ 4% Rh; Rh/Mo = 1 | 100 | 0 |
| F | 180 | IrRe/CBV780 4% Ir; Ir/Re = 1 | 100 | 0 |
| G | 180 | IrRe/TiO$_2$ 4% Ir; Ir/Re - 1:1 | 100 | 0 |
| H | 250 | RhMo/TiO$_2$ 4% Rh; Rh/Mo = 1 | 100 | 0 |
| J | 250 | RhZr/Celite 4% Rh; Rh/Zr = 2 | 100 | 0 |
| K | 180 | Fe/WO$_3$ 10% Fe | 0 | 0 |
| L | 140 | WOx | 0 | 0 |
| M | 140 | Pt/SiO$_2$ 4% Pt | 0 | 0 |
| N | 140 | Pt/Al$_2$O$_3$ 4% Pt | 0 | 0 |
| P | 140 | W/Al$_2$O$_3$ 4% W | 0 | 0 |
| Q | 140 | PtW/MgO 4% Pt Pt/W = 1 | 0.5 | 0 |
| R | 140 | PtW/NbO 4% Pt Pt/W = 1 | 0 | 0 |

Comparative Examples S, T, and V

Comparative Examples S, T, and V were performed following the procedure of Examples 83-190 except using 180° C., the catalysts shown in Table 19, and 2-hydroxymethyltetrahydropyran as the substrate instead of 126HT. The catalysts used in these Comparative Examples contained 4 weight percent Pt and were prepared according to Catalyst Preparation Method A except that there was no addition of a second metal. The results show that no 16HD was observed in the reaction solutions for Comparative Examples S and T, and selectivity to 16HD was very low for Comparative Example V.

TABLE 19

Results for Comparative Examples S-V.

| Comp Ex | Catalyst (M1/Support) | % Conv | % sel to 1P | % sel to 1H | % sel to 16HD |
|---|---|---|---|---|---|
| S | Pt/Al$_2$O$_3$ | 2.94 | 1.53 | 11.65 | 0 |
| T | Pt/SiO$_2$ | 2.23 | 1.46 | 11.19 | 0 |
| V | Pt/CBV780 | 2.65 | 1.49 | 11.08 | 1.4 |

What is claimed is:

1. A process for preparing an α,ω-C$_n$-diol, comprising the steps:
   (a) providing a feedstock comprising a C$_n$ oxygenate;
   (b) contacting the feedstock with hydrogen gas, in the presence of a catalyst at a temperature and for a time sufficient to form a product mixture comprising an α,ω-C$_n$-diol; wherein n is 5 or greater;
   and wherein the catalyst comprises a metal M1 and a metal M2 or an oxide of M2, and optionally a support, wherein:
   M1 is Rh and M2 is Mo, W, V, Mn, Ni, Cu, Zn, Cr, Ge, Sn, Ti, Au, or Zr.

2. The process of claim 1, wherein n=5 or 6.

3. The process of claim 1 wherein the optional support is present in the catalyst and comprises WO$_3$, SiO$_2$, Al$_2$O$_3$, carbon, TiO$_2$, ZrO$_2$, SiO$_2$—Al$_2$O$_3$, montmorillonite, SiO$_2$—TiO$_2$, tungstated ZrO$_2$, zeolites, V$_2$O$_5$, MoO$_3$, or mixtures thereof.

4. The process of claim 1 wherein the C$_n$ oxygenate comprises 1,2,6-hexanetriol; 1,2,5-pentanetriol; 2H-tetrahydropyran-2-methanol; tetrahydrofuran-2,5-dimethanol; furan-2,5-dimethanol; 2,5 dihydrofuran-2,5-dimethanol; levoglucosenone; levoglucosan; levoglucosenol; 1,6-anhydro-3,4-dideoxy-p-D-pyranose-2-one; isosorbide; hydroxymethylfurfural; sorbitol; glucose; fructose; xylitol; 3,4-dihydro-2H-pyran-2-carbaldehyde; 1,2,5,6-hexanetetraol; 1,2,3,5,6-hexanepentanol; 1,5-anhydro-3,4-dideoxyhexitol; 5-hydroxy-2H-tetrahydropyran-2 methanol; furfural; furfuryl alcohol; tetrahydrofurfuryl alcohol; pentoses; dimers containing pentose; oligomers containing pentose; hexoses; dimers containing hexose; oligomers containing hexose; condensation products from the reaction of 5-(hydroxymethyl)-2-furfural ("HMF") with ketones and/or aldehydes, and condensation products from the reaction of furfural with ketones and/or aldehydes.

5. The process of claim 4, wherein the C$_n$ oxygenate comprises 1,2,6-hexanetriol; 2H-tetrahydropyran-2-methanol; tetrahydrofuran-2,5-dimethanol; levoglucosenone; 3,4-dihydro-2H-pyran-2-carbaldehyde, or mixtures thereof.

6. The process of claim 5, wherein the C$_n$ oxygenate comprises 1,2,6-hexanetriol.

7. The process of claim 4, wherein the C$_n$ oxygenate comprises 1,2,5-pentanetriol; furfural; furfuryl alcohol; tetrahydrofurfuryl alcohol; xylitol; or mixtures thereof.

8. The process of claim 1, further comprising the steps:
   (c) optionally, isolating the α,ω-C$_n$-diol from the product mixture;
   (d) contacting the α,ω-C$_n$-diol with ammonia and hydrogen in the presence of a reductive amination catalyst at a temperature and for a time sufficient to form a second product mixture comprising an α,ω-C$_n$-diaminoalkane; and
   (e) optionally, isolating the α,ω-C$_n$-diaminoalkane from the second product mixture.

9. The process of claim 8, wherein the α,ω-C$_n$-diaminoalkane comprises 1,6-diaminohexane.

10. The process of claim 9 wherein the C$_n$ oxygenate comprises 1,2,6-hexanetriol; 1,2,5-pentanetriol; 2H-tetrahydropyran-2-methanol; tetrahydrofuran-2,5-dimethanol; furan-2,5-dimethanol; 2,5 dihydrofuran-2,5-dimethanol; levoglucosenone; levoglucosan; levoglucosenol; 1,6-anhydro-3,4-dideoxy-p-D-pyranose-2-one; isosorbide; hydroxymethylfurfural; sorbitol; glucose; fructose; xylitol; 3,4-dihydro-2H-pyran-2-carbaldehyde; 1,2,5,6-hexanetetraol; 1,2,3,5,6-hexanepentanol; 1,5-anhydro-3,4-dideoxyhexitol; 5-hydroxy-2H-tetrahydropyran-2 methanol; furfural; furfuryl alcohol; tetrahydrofurfuryl alcohol; pentoses; dimers containing pentose; oligomers containing pentose; hexoses; dimers containing hexose; oligomers containing hexose; condensation products from the reaction of 5-(hydroxymethyl)-2-furfural ("HMF") with ketones and/or aldehydes, and condensation products from the reaction of furfural with ketones and/or aldehydes.

\* \* \* \* \*